US009711033B2

(12) United States Patent
Henniges et al.

(10) Patent No.: US 9,711,033 B2
(45) Date of Patent: Jul. 18, 2017

(54) SYSTEM AND METHOD FOR COLLECTING MEDICAL WASTE THAT MONITORS THE WASTE FOR OBJECTS THAT MAY HAVE BEEN INADVERTANTLY DISCARDED

(71) Applicant: Stryker Corporation, Kalamazoo, MI (US)

(72) Inventors: Bruce D. Henniges, Galesburg, MI (US); Richard F. Huyser, Kalamazoo, MI (US); Chris Philipp, Portage, MI (US); Dennis Stratton, Plainwell, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 14/751,688

(22) Filed: Jun. 26, 2015

(65) Prior Publication Data

US 2015/0332577 A1      Nov. 19, 2015

Related U.S. Application Data

(60) Division of application No. 12/955,275, filed on Nov. 29, 2010, now Pat. No. 9,089,318, which is a
(Continued)

(51) Int. Cl.
| | | |
|---|---|---|
| *G08B 13/14* | (2006.01) | |
| *G08B 21/18* | (2006.01) | |
| *A61G 12/00* | (2006.01) | |
| *B62B 3/10* | (2006.01) | |
| *B65F 1/14* | (2006.01) | |

(Continued)

(52) U.S. Cl.
CPC ............ *G08B 21/182* (2013.01); *A61B 50/10* (2016.02); *A61B 50/24* (2016.02); *A61B 50/36* (2016.02);
(Continued)

(58) Field of Classification Search
CPC . A61B 19/0287; A61B 19/0248; A61B 50/10; A61B 50/24; A61B 50/36;
(Continued)

(56) References Cited

U.S. PATENT DOCUMENTS

| | | |
|---|---|---|
| 440,073 A | 11/1890 | Bush |
| 3,412,965 A | 11/1968 | Alexander |

(Continued)

FOREIGN PATENT DOCUMENTS

| | | |
|---|---|---|
| GB | 2 426 490 A | 11/2006 |
| JP | H11-179100 A | 7/1999 |

(Continued)

OTHER PUBLICATIONS

EPO "Search Report for EP 09767418.8" dated Mar. 3, 2014.
(Continued)

*Primary Examiner* — Thomas Mullen

(57) ABSTRACT

A mobile cart that holds a bag for receiving solid waste generated during a medical or surgical procedure. The cart includes a sensor that monitors whether or not an object containing metal is placed in the bag. A processor monitors the signal output by the sensor. If the sensor signal indicates that an object with a minimal amount of metal is placed in the bag, the processor momentarily asserts an audible alarm and continuously asserts a light alarm. The light alarm remains asserted until turned off. If, while the light alarm is on, the sensor signal indicates a second object with the minimal amount of waste is placed in the container, the processor again momentarily asserts the audible alarm. This provides notice that it may be necessary to investigate the contents of the bag to determine if not one but two or more objects were inadvertently discarded.

17 Claims, 17 Drawing Sheets

Related U.S. Application Data continuation of application No. PCT/US2009/045668, filed on May 29, 2009.

(60) Provisional application No. 61/057,666, filed on May 30, 2008.

(51) Int. Cl.
  *B65F 1/10* (2006.01)
  *A61B 50/10* (2016.01)
  *A61B 50/24* (2016.01)
  *A61B 50/36* (2016.01)
  *A61B 50/30* (2016.01)
  *A61B 90/00* (2016.01)

(52) U.S. Cl.
  CPC ............ *A61G 12/001* (2013.01); *B62B 3/106* (2013.01); *B65F 1/10* (2013.01); *B65F 1/1415* (2013.01); *A61B 2050/314* (2016.02); *A61B 2090/0804* (2016.02); *A61B 2090/0805* (2016.02); *B65F 1/1473* (2013.01); *B65F 2210/1125* (2013.01); *B65F 2210/1525* (2013.01); *B65F 2210/167* (2013.01); *B65F 2210/184* (2013.01); *B65F 2240/145* (2013.01)

(58) Field of Classification Search
  CPC .......... B62B 3/106; B65F 1/10; B65F 1/1415; G08B 21/182; A61G 12/001
  USPC ......... 340/568.1, 572.1, 686.4; 604/317–319
  See application file for complete search history.

(56) References Cited

U.S. PATENT DOCUMENTS

| | | |
|---|---|---|
| 3,893,699 A | 7/1975 | Morris |
| 4,124,185 A | 11/1978 | Preisinger |
| 4,448,434 A | 5/1984 | Anderson |
| 4,637,545 A | 1/1987 | Stewart |
| 4,809,915 A | 3/1989 | Koffsky et al. |
| 4,917,393 A | 4/1990 | Rogers |
| 4,979,706 A | 12/1990 | Feldman et al. |
| 5,001,425 A | 3/1991 | Beling et al. |
| 5,195,649 A | 3/1993 | Wolters |
| 5,339,959 A | 8/1994 | Cornwell |
| 5,445,398 A | 8/1995 | Pierce |
| 5,576,621 A | 11/1996 | Clements |
| 5,659,247 A | 8/1997 | Clements |
| 6,045,264 A | 4/2000 | Miniea |
| 6,126,183 A | 10/2000 | Lensing |
| 6,222,450 B1 | 4/2001 | Clements |
| 6,352,225 B1 | 3/2002 | Dooley et al. |
| 6,375,131 B1 | 4/2002 | Youst |
| 6,651,942 B1 | 11/2003 | Yardley et al. |
| 6,833,789 B1 | 12/2004 | Carmen et al. |
| 7,114,629 B2 | 10/2006 | Panek |
| 7,484,275 B2 | 2/2009 | Carroll et al. |
| 2003/0164600 A1 | 9/2003 | Dunn et al. |
| 2004/0000904 A1 | 1/2004 | Cotter |
| 2004/0222335 A1 | 11/2004 | Panek |
| 2008/0015898 A1 | 1/2008 | Mallett et al. |
| 2010/0201090 A1 | 8/2010 | Henniges et al. |

FOREIGN PATENT DOCUMENTS

| | | |
|---|---|---|
| JP | 2003-044947 A | 2/2003 |
| JP | 2006-209350 A | 8/2006 |
| JP | 2007-067598 A | 3/2007 |

OTHER PUBLICATIONS

"Response to EP Search Report for EP 09767418.8" dated Feb. 14, 2011.

PCT"International Search Report and Written Opinion" for PCT/US2009/045668, dated Jan. 13, 2010.

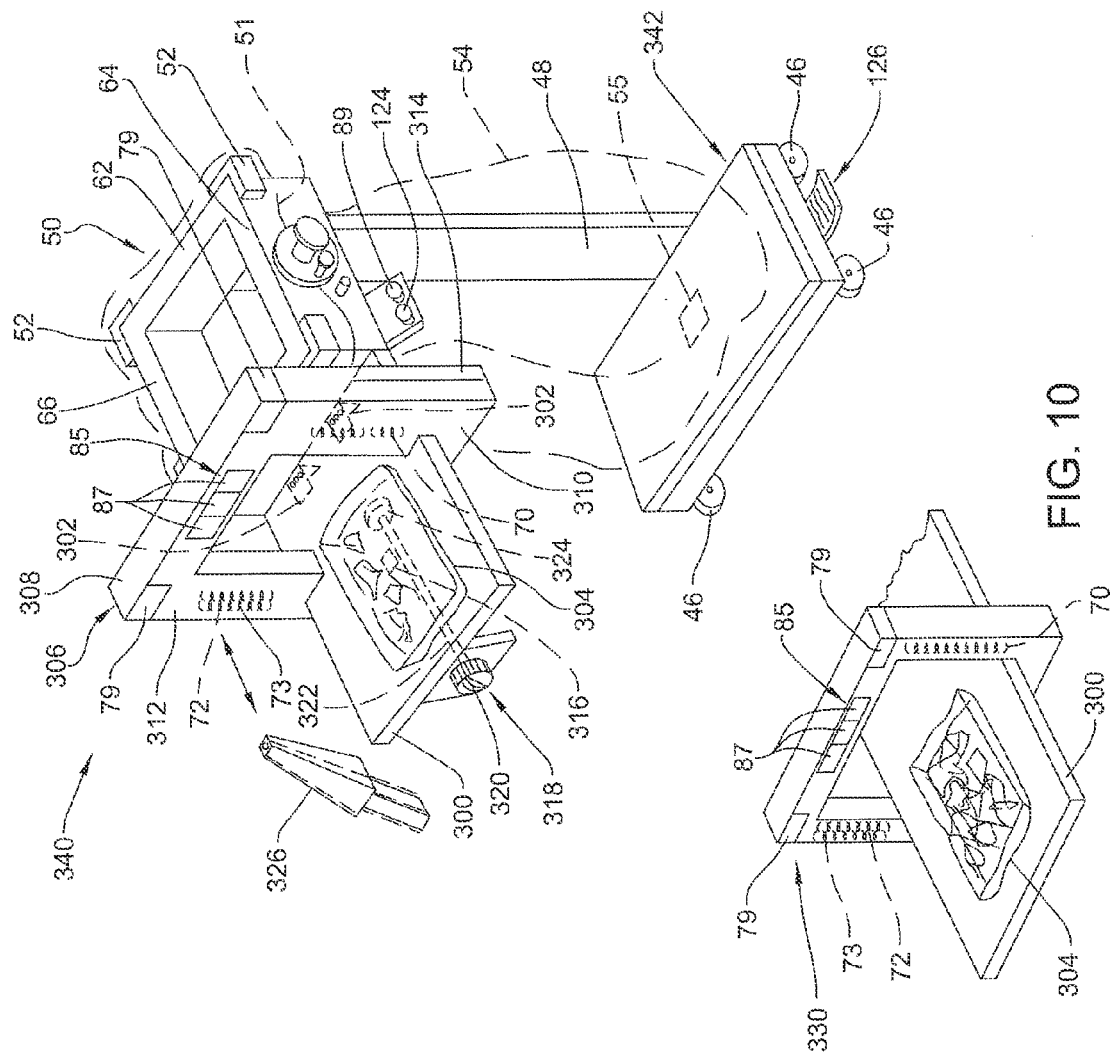

SYSTEM AND METHOD FOR COLLECTING MEDICAL WASTE THAT MONITORS THE WASTE FOR OBJECTS THAT MAY HAVE BEEN INADVERTANTLY DISCARDED

RELATIONSHIP TO EARLIER FILED APPLICATIONS

This application is a divisional of U.S. patent application Ser. No. 12/955,275 filed 29 Nov. 2010 now U.S. Pat. No. 9,089,318 B2. Application Ser. No. 12/955,275 is a continuation of PCT App. No. PCT/US2009/045668 filed 29 May 2009. PCT App. No. PCT/US2009/045668 is a non-provisional of U.S. Provisional Pat. App. No. 61/057,666 filed 30 May 2008. The earlier filed applications are incorporated herein by reference.

FIELD OF THE INVENTION

The present invention relates generally to a system for collecting and temporarily storing solid medical waste. More particularly, the present invention is directed to a system comprising detection features for reducing inadvertent disposal of reusable medical equipment, tools, and accessories and bag retention features for securing bags to carts used for collecting waste.

BACKGROUND OF THE INVENTION

When a medical or surgical procedure is performed, solid waste is typically generated. Generally, this type of waste falls into one of several categories. First, there is conventional trash. This type of waste includes solid articles such as paper, plastics and other packaging material that is not contaminated with tissue or bodily fluids. This waste is typically deposited in white or clear bags. A second type of waste, although not truly "waste", is the linens, towels and sheets used during the procedure. These linens, towels and sheets, are used for such purposes as stabilizing the patient, draping off portions of the patient, or cleaning up liquids. Often these materials, even those covered in body fluids, can be cleaned, sterilized, and reused. This type of waste is typically deposited in green bags. A third type of solid waste includes solid articles that, during the procedure become coated or exposed to bodily fluids. These articles include disposable wipes, gloves and drapes used at or around the surgical site as well as single use disposable medical instruments. Post use, these articles are disposed of in a manner that ensures the biological material they carry does not serve as a source of infection. It is also important to prevent contamination of medical personnel and the medical facility when handling or transporting this waste materials. Often, this material is called "red bag" waste because it is typically deposited in specially marked red bags. A fourth type of solid waste is radioactive waste typically deposited in yellow bags.

During the course of a procedure, solid medical waste is deposited in the corresponding bags secured to portable carts in the operating room or other space in which they are generated. In some medical facilities, separate carts are provided for collection and storing the different types of medical waste as described above. The circulating nurse or other individual responsible for initially disposing of the waste, initially categorizes the waste and places the waste in the appropriate bag on a cart. When a bag containing either conventional waste, red bag waste, or radioactive waste is at or near capacity, it is sealed. At that time, the bag is transported to a loading dock for eventual transport to a waste processing facility. Green bag waste is transported to a processing facility where the linens, towels and sheets are cleaned and sterilized for reuse.

With the advent of packaged sterile goods, the amount of solid medical waste generated has increased. This is particularly true of packaged sterile equipment that takes the place of a reusable piece of equipment, tool, or accessory. The acceptance of packaged sterile goods and new medical technologies and procedures has increased the amount and bulk of materials entering the waste stream. This has also increased the chances of reusable medical equipment inadvertently entering the waste stream. Specifically, budgets for purchasing lost reusable equipment have increased over time due to the reusable equipment that is lost or inadvertently thrown away. When certain high value medical equipment has come up missing, some hospitals have mandated that their workers do physical searches of bags of trash entering the waste stream with hopes to find the lost equipment. This solution is not practical, not desirable and also possesses risks to the workers assigned to find the equipment. One important risk involves the exposure of the worker to biologically contaminated waste when searching the "red bag" for inadvertently lost equipment.

A reusable medical device, due to its service life expectations, contains durable components, many of them metal. As a result, such equipment can be detected with appropriately designed metal detection systems. The metal detection system then alerts the worker that a metal-containing piece of equipment, tool, or accessory has been deposited in a waste bag.

Metal detection systems are available in many different forms and can be used to assist a searcher in finding lost metallic items. Some systems employ a metal detector for detecting metal after the waste bags have been filled with waste. The obvious shortcomings of these systems include requiring workers to maneuver often heavy, full bags of trash. What's more, if metal is detected, the worker must then rummage through a full bag of trash to uncover the item. Many times the item found in the trash was a single use disposable manufactured with metallic components and therefore may have been correctly deposited in the bag after all. For instance, there are several single use disposable items with metallic components like motors or batteries that will be detected. Additionally, the bags are usually tied shut and are difficult to open making the worker's task even more difficult.

Further, it should be appreciated that biological materials can include contaminates and transmit infectious diseases. Accordingly, the individuals handling bags containing these materials run the risk of inadvertent exposure to these contaminates. Also, an appreciable fraction of these biological materials are in the liquid state. These fluids have been known to leak out of a bag during handling. Also, when in the liquid state, these biological materials, and their associated contaminates, have been known to become aerosolized. When this happens, the surrounding environment can become contaminated. This increases the risks of transmission to more persons other than those responsible for handling the bags. These hazards considerably increase when workers search for reusable equipment or other metallic items mixed in infectious or hazardous waste.

Another proposed solution is metal detection at the point of disposal. Known waste carts typically include a barrel for holding the waste bags and a metal detector ring for placing on top of the barrel over the bag. In these systems, when a metal-containing object is discarded, an alarm is tripped requiring the user to look inside the bag for the metal-containing object. As previously described, this is less than desirable during a medical or surgical procedure. If the bag is partially or nearly full of medical waste, the metal-containing article may slip to the bottom of the waste bag when the worker shifts the medical waste in the bag looking for the metal-containing object. Additionally, sterile personnel performing a medical procedure cannot search the contents of the waste containers without breaking sterility.

Since the metal detector ring accumulates dust and biological materials due to the medical detector ring being on top of the barrel and waste bag, the metal detector ring must be cleaned between uses. Also, metal detection on these prior art systems may not be tunable to vary the amount of metallic content that triggers the alarm. Thus, with the increase in disposable medical equipment, tools, and accessories, some of these prior art systems are unable to selectively set alarm conditions and reduce false alarms.

Securing waste bags to conventional waste carts is often cumbersome. Some workers tie a knot in the top of the waste bag to reduce the size of the opening. The bag is then stretched over a hoop of the waste cart to secure the bag to the waste cart. This method is time consuming and not always predictable.

The Applicants' Assignee's U.S. Provisional Patent Application No. 60/980,964, SYSTEM AND METHOD FOR COMPACTING SOLID MEDICAL WASTE, filed 18 Oct. 2007, the contents of which are contained in PCT App. No. PCT/US2008/080170, filed 16 Oct. 2008, published as WO 2009/052291 A1 and US Pat. Pub. No. US 2010/0201090 A1, both of which are hereby incorporated as reference, discloses one alternative system for collecting medical waste and, during the collection process, determining if an article formed from metal is being inadvertently discarded.

However even the above system has disadvantages associated with its use. These disadvantages are associated with how a bag is secured to the frame of the system of WO 2009/052291 A1 and US Pat. Pub. No. US 2010/0201090 A1 and how this system informs medical/surgical personnel that a metal item may have been inadvertently discarded.

SUMMARY OF THE INVENTION

This invention is directed to a new and useful system for holding solid waste such as the waste generated during a medical/surgical procedure. The system of this invention includes a mobile base that holds a bag, a container, for collecting waste. In some versions of the invention, a frame, from which the bag is suspended, contains a sensor assembly for detecting if metal objects are passed through the open end of the bag. A processor monitors the signals emitted by the sensor. In the event the sensor signals indicate an article with a substantial content of metal is placed in the bag, the processor actuates both an audible alarm and a light. The audible alarm is actuated only for a short time. The light is actuated until the system is reset by the medical/surgical personnel.

The system of this invention also includes a tensioner that holds the bag tight to the frame. When it is desired to remove the bag, the tensioner is released.

In some versions of this invention, the cart has an escrow hold. The waste is placed in initially placed in the escrow hold. Sensors around the escrow hold determine if the waste contains metal. If there is no metal in the waste, the waste is automatically transferred to the bag. Alternatively, if sensors detect the presence of waste in the escrow hold, the alarms are actuated. This provides the personnel the opportunity to remove any metal objects that may have inadvertently placed in the system.

BRIEF DESCRIPTION OF THE DRAWINGS

Advantages of the present invention will be readily appreciated as the same becomes better understood by reference to the following detailed description when considered in connection with the accompanying drawings wherein:

FIG. 9 is a side perspective view of a frame of the cart of the present invention, the cart be outfitted with another pre-detection apparatus;

FIG. 10 is a side perspective view of a portion of the frame of the cart outfitted with another pre-detection apparatus of this invention;

DETAILED DESCRIPTION

Figure 1:
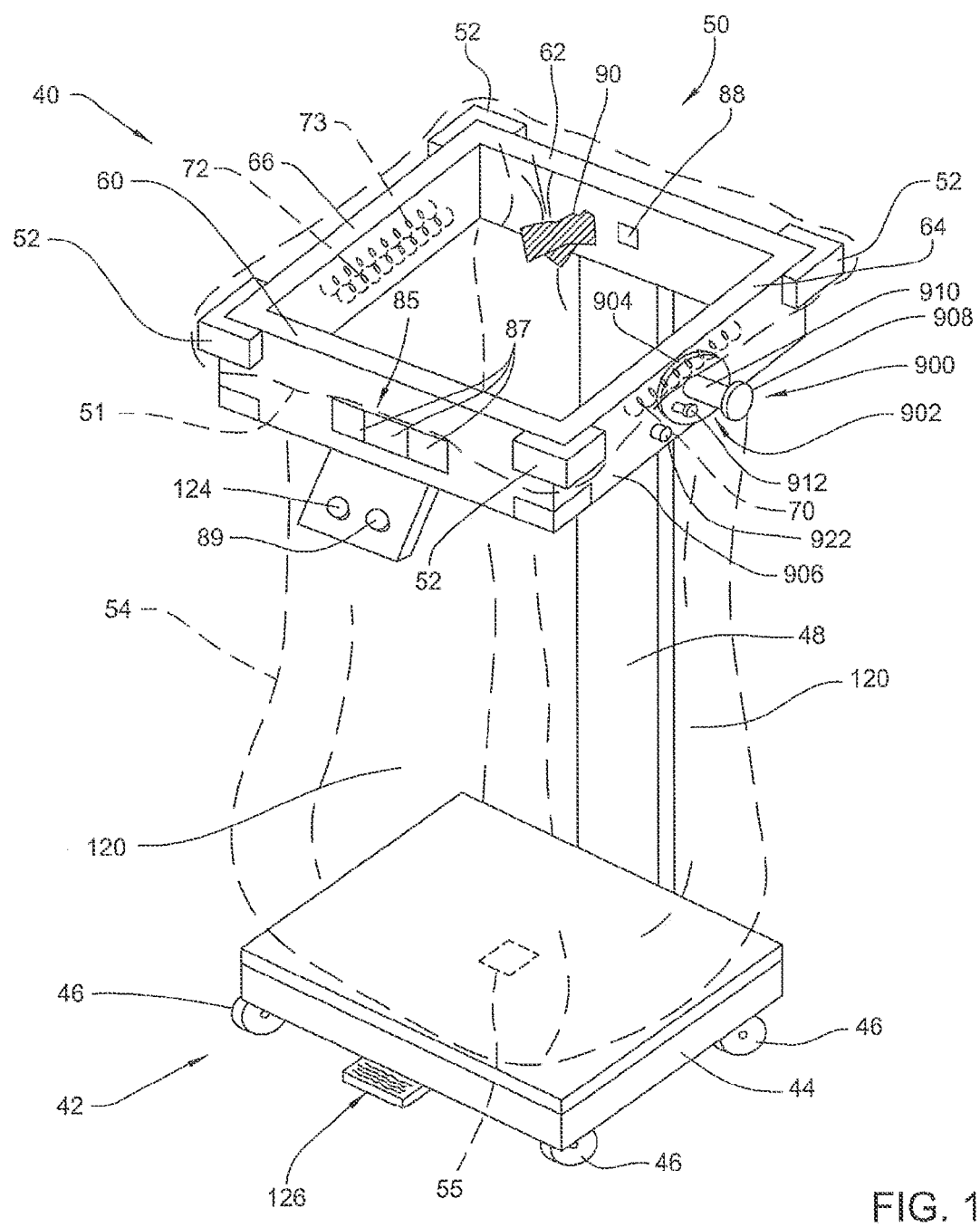
FIG. 1 is a perspective view of a cart of the present invention, the view being of the front of the cart.

Referring to the Figures, wherein like numerals indicate like or corresponding parts throughout the several views, a solid medical waste collection system is generally shown at 40 in FIG. 1. The system is particularly adapted for collecting solid medical waste during medical or surgical procedures, but is not limited to this purpose. Such waste may include: (1) conventional trash; (2) used linens, towels and sheets; (3) solid articles coated or exposed to bodily fluids; (4) and radioactive waste.

Referring to FIG. 1, the system 40 comprises a cart 42 with a planar base 44. Casters 46 are mounted to a bottom of the base 44 to provide the cart 42 with mobility. A rectangular leg 48 extends upwardly from one side of the base 44. The leg 48 suspends an open rectangular frame 50 above the base 44.

The frame 50 is formed from plastic or other material that does not affect the transmission of electromagnetic waves. The frame 50 comprises front 60 and rear 62 webs and front-to-rear extending lateral webs 64, 66 interconnecting the front 60 and rear 62 webs. The front 60 and rear 62 webs of the frame 50 are longer than the associated front-to-rear extending lateral webs 64, 66.

A plurality of corner blocks 52 project outwardly from outer surfaces of the frame 50. The blocks 52 act as retaining members that hold an open periphery 51 of a bag 54 disposed in the frame 50 and supported by the base 44. When the periphery 51 of the bag 54, sometimes referred to as a container, is stretched and folded over the frame 50 and the blocks 52, the periphery 51 is held under the blocks 52. The blocks 52 protrude outwardly from corners of intersecting, adjacently connected webs 60, 62, 64, 66.

The bag 54 is preferably formed from a plastic that creates an air-tight barrier. Plastics from which the bag 54 can be formed include polyethylene, polypropylene or nylon. The bag 54 is formed to have two opposed rectangular body panels 120. Bottom and side edges of the body panels 120 are sealed together.

In some embodiments, the base 44 includes a pressure sensitive transducer 55 for determining a weight of the bag 54 as the bag 54 is filled with waste. This feature and a base incorporating this feature are described in the incorporated by reference WO 2009/052291 A1 and US Pat. Pub. No. US 2010/0201090 A1.

Metal detection coils in some embodiments of this invention are arranged with detection coil 72 and null coil 73 that are together oppositely disposed to transmit coil 70. According to FIG. 1, these coils 70, 72, 73 can be disposed in either the front 60 and rear 62 webs or the lateral webs 64, 66 given their opposing orientation. Collectively, coils 70, 72, 73 function as an emitter and sensor assembly that detects when metal is placed through the opening formed by the webs and into the bag 54. Generally, it should be understood that the signal output by the detection coil 72 varies with the amount of metal that passes through frame 60 into the open periphery 51 of bag 54. The above embodiment is different than traditional metal detection coil arrangements.

Traditional metal detection coil arrangements can also be implemented into a cart with suitable geometry. One coil arrangement, called a co-axial arrangement. In the co-axial arrangement, the coils are of similar outside size and shape. The coils 70, 72 and 73 are coaxially aligned and are stacked one on top of the other. The coils are typically arranged with the null coil 73 on top, the transmit coil 70 in the middle and the receive coil 72 on the bottom. These coils are wound in continuous loops with the loops taking a range of shapes like circle, square, rectangle, triangle or hexagonal. In the co-axial arrangement, objects to be detected pass through the inside of the loop. Another coil arrangement known in the art is called concentric coils. In the concentric coil arrangement, the coils typically align to the same axis, but the sizes of the coils are different. In a typical concentric coil arrangement, the center loop coil is the null coil 73, the middle loop is the transmit coil 70 and the outer loop is the detection coil 72. These coils of different perimeter sizes are typically arranged in a planar fashion. This coil arrangement is useful when trying to detect metal that is passed either over or under the plane formed by the concentric perimeters. The perimeter of the concentric coils can also have a different shape such as circular, square, oval or triangular, with the most common shape being circular.

Figure 2:
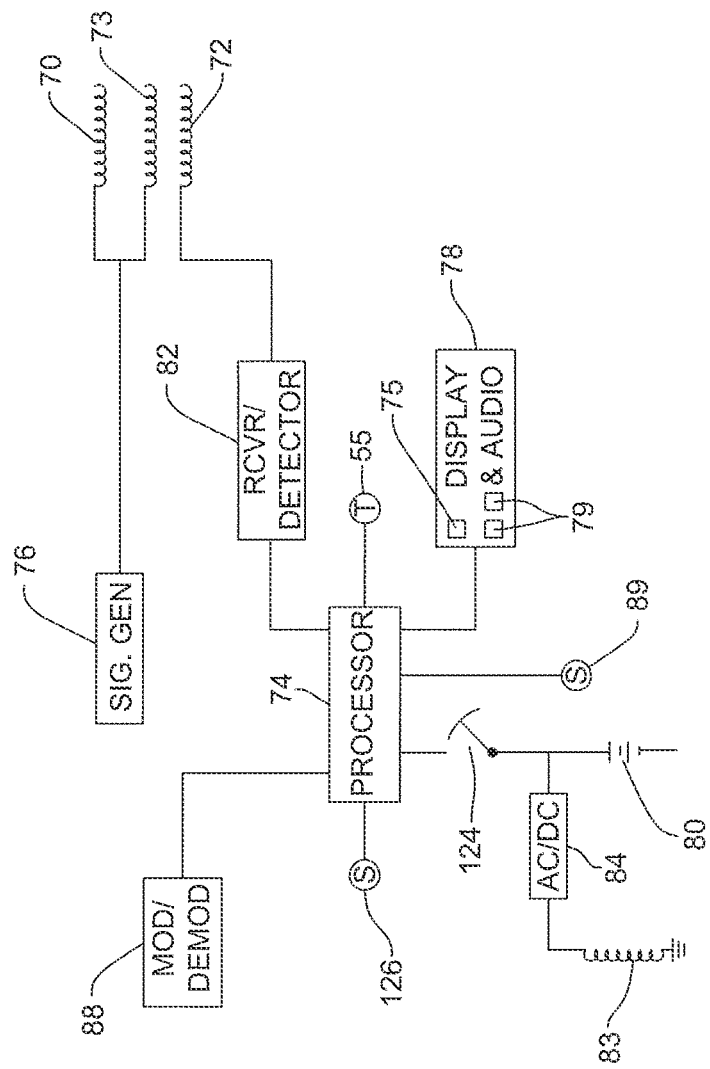
FIG. 2 is a block diagram of the electrical components integral with the cart.

FIG. 2 is a block diagram of circuit components integral with the cart 42. These components include a processor 74. A signal generator 76 generates the AC signal that, as illustrated in FIG. 2, is applied to both the transmit coil 70 and the null coil 73. The signal applied to null coil 73 is typically out of phase with the signal applied to the transmit coil so as to normally cancel out the signal output by the transmit coil 70. Unless metal, when passing through the frame 50 disrupts both signals, ideally no signals are developed across detection coil 72. Cart 42 also has a display 78. In some embodiments an annunciator 75, e.g., an audible alarm, is integral with the display 78. In some embodiments of the invention, one or more separately actuated lights 79 are attached to the corners of the frame 50 and form part of the display 78.

In some embodiments, a light bar 85, seen in FIG. 1, with a plurality of separately actuated light segments 87 indicates the strength of the signal generated by detection coil 72. While not shown, it should be understood that processor 74 regulates the actuation of the light segments 87. In some configurations of this invention, the number of light segments 87 that processor 74 actuates is proportional to the amount of metal detected passing through the frame 50 as determined based on the analysis of the signal output by detection coil 72. Only one segment 87 is illuminated if signal analysis indicates only a small amount of metal is passed into the bag 54. Plural light segments 87 are illuminated if signal analysis indicates that there may have been a large amount of metal placed in the bag. This feature is useful to quickly determine the relative metal content of the objects discarded in the bag 54.

The user sets the threshold of detected metal at which the alarm should be asserted with a sensitivity selector 89. The selector 89 could be any number of different input types, potentiometer dial or knob with multiple settings, switch with two settings, etc. The state of the signal output by selector 89 is monitored by the processor 74 to determine the user's desired setting. Based on this setting, processor 74 determines when the signal output by the detection coil reaches the level at which the alarms should be asserted. This threshold adjustment reduces the assertion nuisance alarms due to the presence of foil packages or low metal content single use disposable items in the waste stream.

In some embodiments, the threshold of metal detection can be set such that the audible alarm does not sound until the metal content signal is above a predetermined level, such as at a level that would illuminate all three segments 87 of the light bar 85. The light bar 85 shows the user the relative metal content. The audible alarm is only asserted when an article with sufficient metal to cause all three light segments of the level indicator to be illuminated is deposited in the bag 54. When two or less segments 87 are illuminated, there is no audible alarm. The processor 74 may include a counter (not shown) that counts the number of objects that are discarded in each segment category, e.g., number of objects that illuminate one segment 87, two segments 87, etc. The processor 74 then stores the information for later reporting. The reporting can be used to adjust the system settings to minimize improper discarding of objects, while minimizing inconvenience to personnel. The illuminated light segments can be used as a gage for the users to determine what level to set the alarms. For example, if a reusable scalpel handle when passed by the metal detection coils illuminates two segments 87, the user can decide to set the alarms to detect the reusable scalpel handle.

A battery 80 powers the components internal to the cart 42. In most versions of the invention, the battery 80 comprises a set of rechargeable cells. Not illustrated is the voltage regulator(s) that output signals at the potentials required by the power consuming components integral with the cart 42. Also not illustrated are all the connections from the battery 80 to which the power sourced by the battery 80 is applied. These rechargeable cells can be charged with a built-in charger, or alternately charged with an independent charger; neither of the chargers are shown in the figures.

Also internal to the cart 42 is a receiver 82. The receiver 82 is connected to the second coil 72 to convert the signals developed across the second coil 72 into a form in which they can be processed by processor 74. The signal produced by transducer 55 is also applied to processor 74 as in input signal. Not illustrated are any amplifiers needed to amplify the signal from the transducer 55 prior to application to the processor.

As described above, and in U.S. Provisional App. No. 60/980,954, coil 83 may also form part of the circuit internal to the cart 42. The coil 83 is a coil configured to receive energy that is inductively transmitted to the cart 42. As described above, the cart 42 may incorporate features for trash compaction and may be periodically placed in a compactor (not shown) that compresses the waste in the bag 54. When the cart 42 is so positioned, a current is sourced from the compactor to the cart 42 to recharge the batteries 80. An AC/DC circuit 84 is shown as being connected between coil 83 and the battery 80. The AC/DC circuit 84 converts the AC signal developed across coil 83 into a DC signal that charges the batteries 80.

Figure 4:
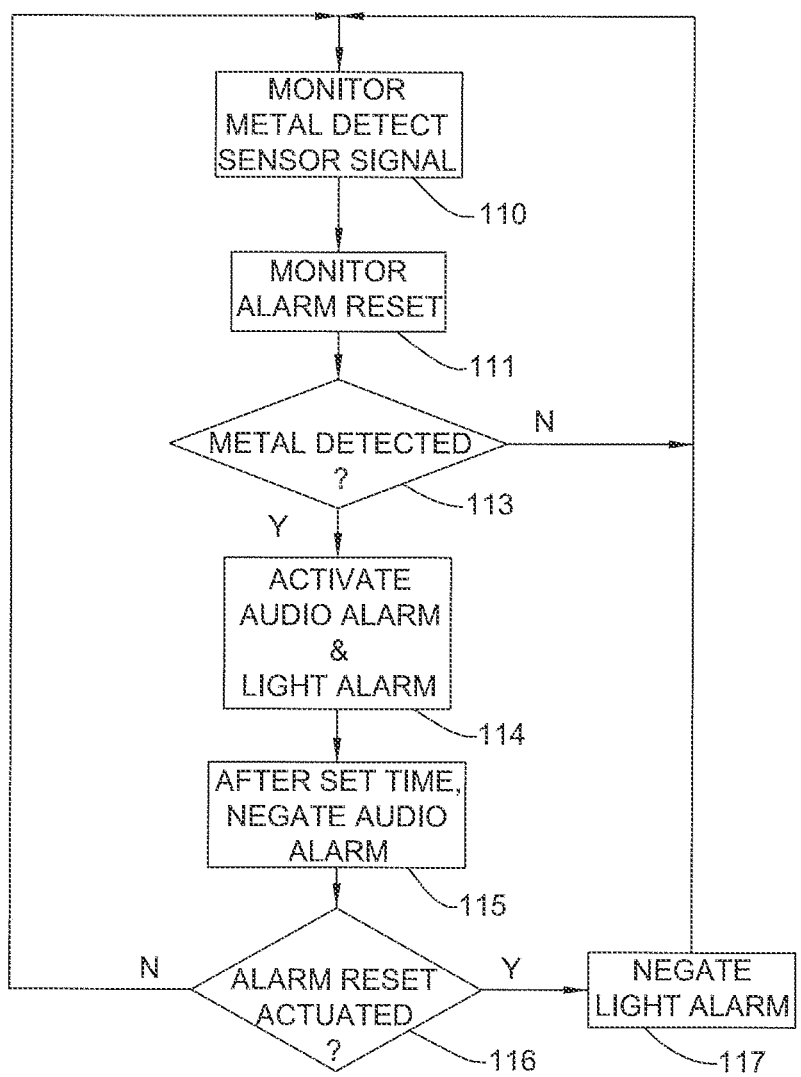

Processor 74 monitors the signals output by the transducer 55 and coil 72. The processor 74 monitors the signal that develops across the coil 72 to determine if there is rapid change in the signal. FIG. 4 illustrates steps of metal detection and alarm. Step 110 of FIG. 4 represents the continual monitoring of the signal from coil 72, the metal detect sensor. Step 111 represents the continual monitoring of a manually actuated alarm reset switch 126 (FIG. 4) the purpose of which is discussed below.

Processor 74 compares the signal output by coil 72, the signal obtained in step 110, to a reference level. Again, the reference level is set based on the user-entered setting of sensitivity selector 89. Based on the comparison, represented by step 113, the processor 74, determines whether or not the sensor has generated a signal indicating it is likely that metal has passed through the frame 50 into the bag 54. In some versions of the invention, the sensor signal that is analyzed is an average signal. The average may be taken over a period ranging from 10 microseconds to a second. The comparison may be to an average signal to reduce the likelihood that, due to noise in the sensor signal, processor incorrectly interprets a change in signal strength as indicating the passing of metal in the bag 54. The loop back from step 113 to step 110 indicates that steps 110, 111, 112 and 113 are continually executed.

If the analysis of step 113 indicates that the presence of metal has been detected, in step 114 processor 74 actuates both the audio alarm and the light alarm. This means annunciator 75 and lights 79 and/or 87 are actuated. After a set time, as represented by step 115, processor negates the assertion of the audio alarm. This period is typically under 10 seconds and more typically less than 5 seconds. While processor 74 deactivates the annunciator 78, the processor does continue to assert the control signals that keep lights 79 and/or 87 actuated.

Processor 74 does, however, based on the monitoring of the alarm reset switch 126 of step 111, in a step 116, evaluate whether or not the switch 126 is actuated. Upon determining that the switch 126 has been actuated, in step 117, the processor 74 asserts the signals that result in the turning off of the lights 79 and/or 87, the negation of the light alarm. The loop back from when the evaluation of step 116 tests negative to step 110 represents that, as mentioned above, the processor 74 continues to evaluate whether or not objects with a metal content of at least the threshold level are deposited in the bag even while the light alarm 79 remains actuated.

Figure 3:
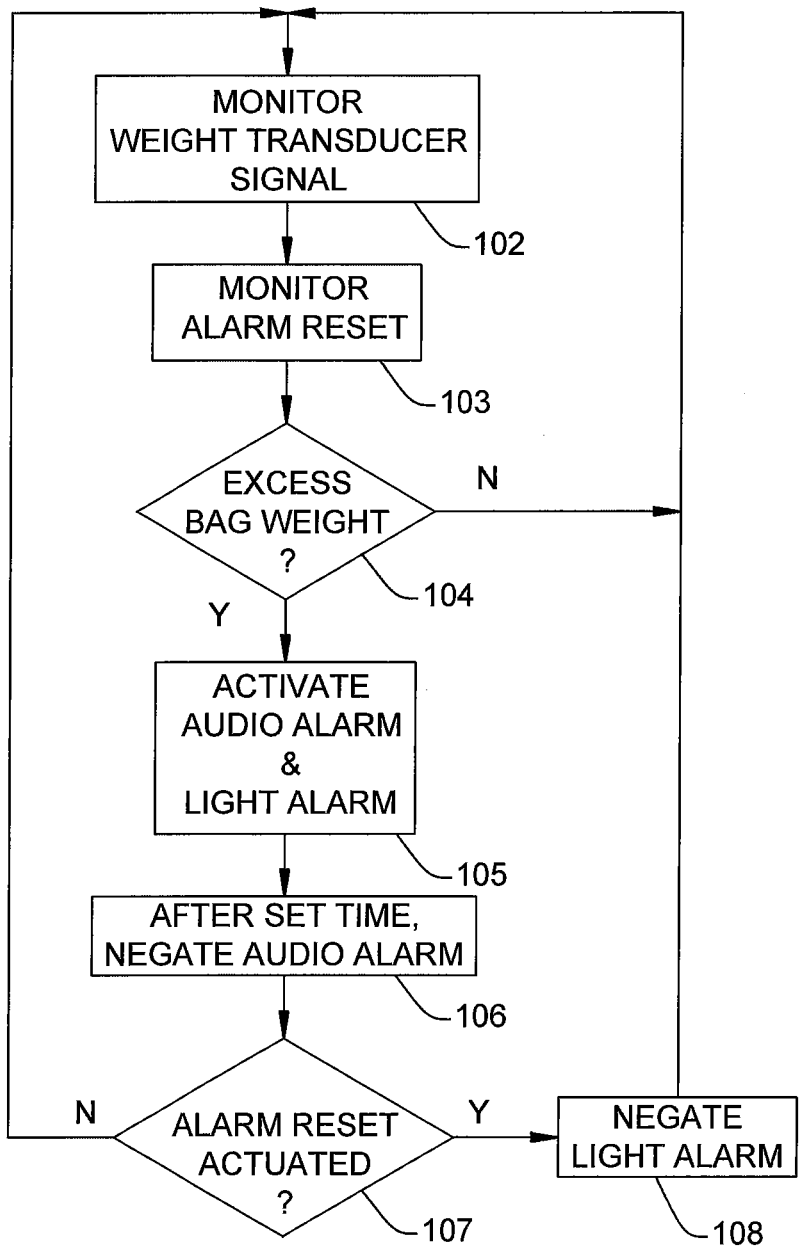
FIGS. 3 and 4 are flow charts depicting steps taken for weight detection and metal detection.

FIG. 3 illustrates steps of weight detection and alarm. The signal output by transducer 55 is related to the weight of the waste contained in the bag 54. When the cart 42 is in use, the processor 74 continually monitors the transducer output signal, as illustrated by step 102. As described above, the processor also continues to monitor whether or the alarm switch 126 is actuated, in FIG. 3 called out as step 103. Processor 74 compares this signal received from transducer 55 to a reference signal level representative of a preferred maximum weight for the bag 54 and its contents, step 104. In the event the comparison in step 104 shows that the bag is not yet full, the above-described monitoring continues.

At times health care workers would be applying external loads that could be registered by the weight transducer 55. For example they could step on the lower platform or be manually compacting the waste in order to get more waste into the bag. To prevent false alarms for this condition, the processor 74 could, in step 104, wait to receive two or more subsequent signals from the transducer 55 that indicate the maximum weight has been exceeded. Only if this event occurs does the processor 74 determine that the cart is in a state in which bag 54 contains weight at or above the preferred maximum level.

If the comparison of step 104 indicates that the bag 54 and its contents are above the preferred maximum weight, processor 74, in step 106, asserts an alarm. As with metal detection, the annunciator 75 asserts both the audio and light alarms, step 105. The audio alarm is deactivated after a short time, step 106. The actuation of lights 79 and/or 87 continues until it is determined in step 107 that alarm reset switch 126 was depressed. At that time, in step 108, the light alarm is negated.

Referring back to FIG. 1, the cart 42 of the system 40 of this invention is prepared for use by fitting the bag 54 to the cart 42. Immediately prior to the medical or surgical procedure to be performed, the cart 42 is activated. This activation means that the signal generator 76 is activated by control switch 124 and the processor 74 actively monitors the signal across coil 72 and the pressure sensed by transducer 55. During the medical/surgical procedure, waste is placed in the bag 54 in a conventional manner.

The assertions of both the audible and light alarms of step 114 provide the medical/surgical personnel with the notice that metal has entered the bag 54. This notice serves as a cue that these personnel may want to verify that the object discarded was not a reusable object that was inadvertently discarded. If the investigation indicates the object was inadvertently discarded, the object can be promptly retrieved before additional waste is piled on top of it.

Alarm reset switch 126 can be a foot pedal movably mounted to the base 44 of the cart 42. By using the foot pedal, the user does not need to break sterility during the medical or surgical procedure to shut off the alarm. Alternately, a shut-off switch can be added to this embodiment. The additional shut-off switch can be located in the top structure of the cart 42 on the opposite side of switch 126. This switch can be added to the outside of front web 60 for example. This position allows the non-sterile circulator in the operating room a more convenient location to control the alarm particularly when the foot switch 126 is facing the sterile surgical field.

Embodiments described herein describe metal detection working at the point of disposal. During use, these point of disposal metal detection systems offer real time information that benefits the ability of someone to discover if reusable medical equipment is inadvertently discarded. As mentioned, there are single use disposable instruments that contain metal and are discarded after a single use. The waste collection system of this invention provides real time information and allows the user to review the real time information provided to his/her expectation as to what should happen when disposing of waste. For example, a small reusable electric power tool used in surgery is clamped on a disposable surgical drape. Post use, the drape may be rolled up for disposal and the tool is rolled into the drape. When the rolled up drape is placed in the appropriate container, the point of disposal metal detection system of this invention asserts an alarm indicating to the medical worker that there is a metal object in the rolled drape. Since the worker's expectation was the only item being disposed of was a drape, the assertion of the alarm alerts the worker that it is now appropriate to investigate the drape in order to determine if another objection is inadvertently entrained in the drape. The information provided in conjunction with the timing of that information allows the worker to efficiently recover and prevent inadvertently discarding a valuable piece of reusable equipment. In another example, the worker is discarding a single use battery powered irrigation system containing a metallic motor. When the worker discards the irrigation system, their expectation was that the alarms would be set off by the metal detection system. Since the alarms met the expectation, the worker could simply reset the alarms without having the need to investigate or dig through the waste container.

Alarms described in these embodiments can be controlled by the processor in different configurations and sequences. For example, the metal detection system could be configured with only a visual or only an audible alarm. Visual alarms can be in the form of the light 79 or a set of lights 79. The audible alarms can be in the form of the annunciator 75. Annunciator 75 can be formed from a piezo-electric buzzer or a more elaborate speaker (not shown). In one preferred embodiment, the metal detection system could be configured with both an audible alarm and a visual alarm. These alarms can be set to provide the alerting function while minimizing the distraction they cause. For example, when the metal detection system processes the signal and determines it is appropriate to assert an alarm, both audible and visual alarms could be actuated. In this example, the audible alarm could sound for a finite time, say 1 second, and then automatically turn off. The lights could stay on until a worker investigates the waste and then actuates the alarm reset switch 126 or other shut-off switch. This mechanization of alarming allows the worker to continue performing some other critical work, like performing a medical procedure, without forgetting to investigate the waste for metallic equipment until there is a more convenient time for that investigation.

During the course of the procedure, the contents of the bag 54 increase in weight and volume. The processor 74, per the steps of FIG. 3, also monitors the weight of the bag 54. If the bag starts to become excessively weighted down, the assertions of the alarms provide notice that it may be appropriate to replace or empty the bag.

Eventually, there is a point in the procedure at which bag 54 is ready for closure. For a particular bag this may be because, as a result of the execution of step 104 it is determined that the bag 54 is full. Alternatively, it may be that the actual medical/surgical procedure is complete and the bag 54, while not full, is ready for short-term storage and transport.

Figure 5:
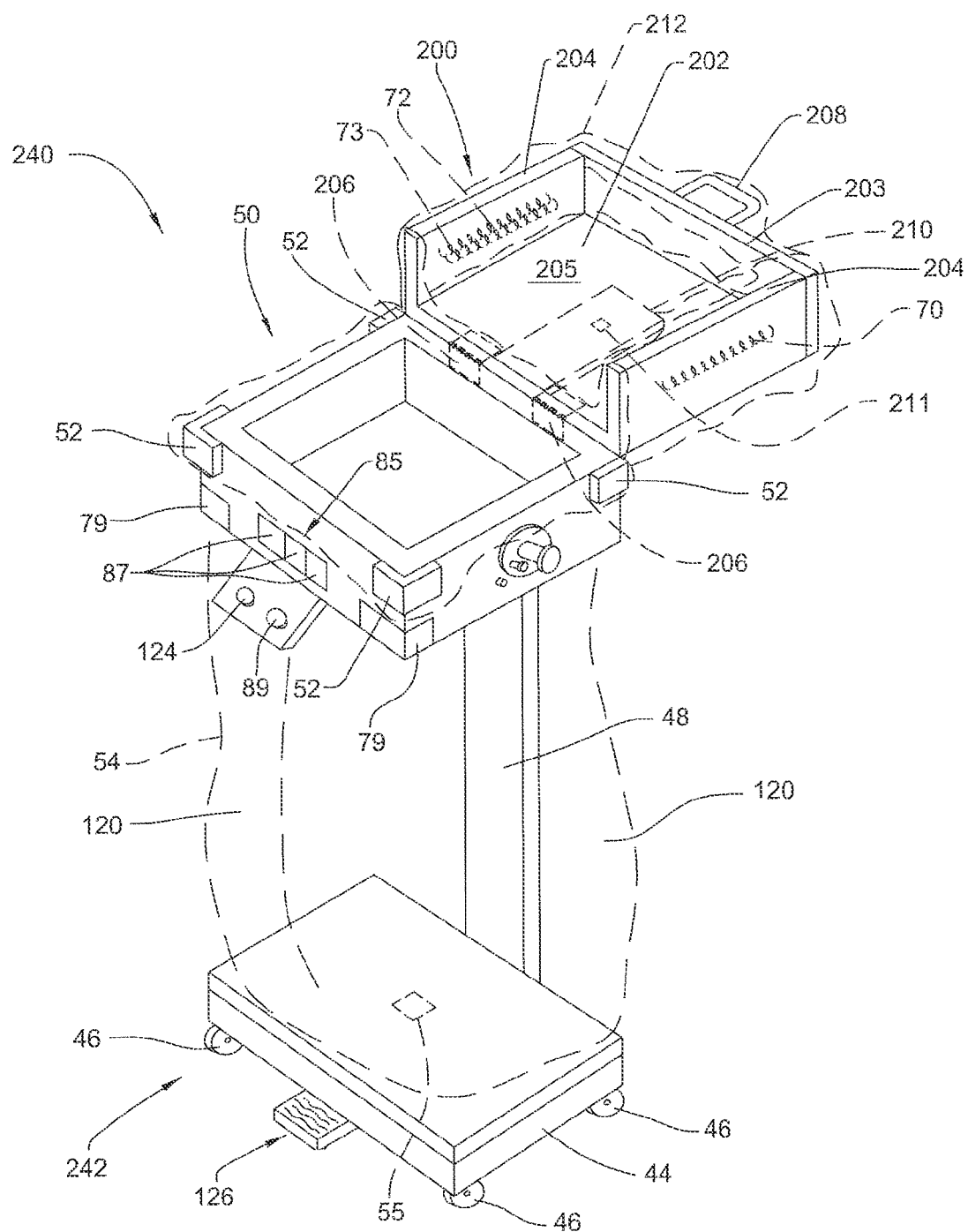
FIG. 5 is a front perspective view of a cart of the present invention with a pre-detection apparatus.
Figure 6:
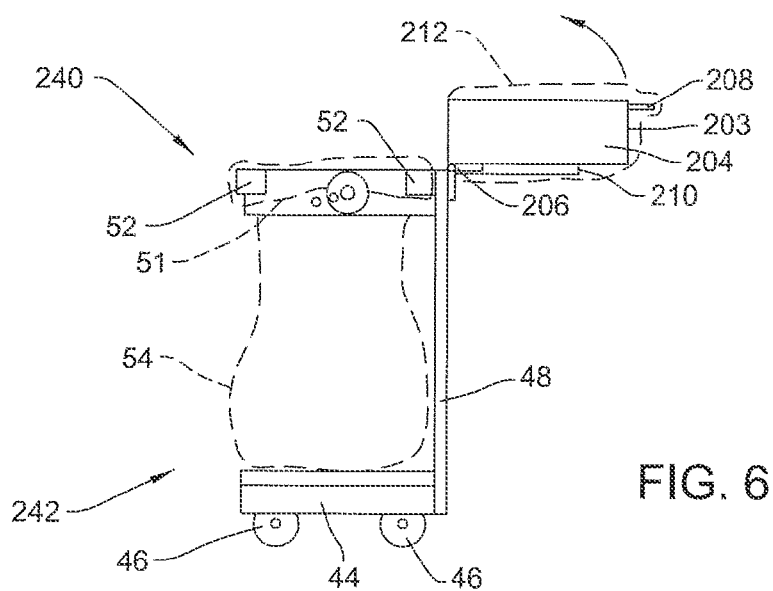
FIG. 6 is a side elevational view of the cart of FIG. 5.

Referring to FIGS. 5 and 6, an alternative system 240 of this invention includes a cart 242 is shown with a pre-detection apparatus for detecting metal-containing objects in batches before being dumped in the bag 54. These batches contain a volume of waste that is only a portion of the entire volume of waste ultimately discarded in the bag 54. Without the pre-detection apparatus, when metal-containing objects are detected by the previously described system 40, the user must sort through existing waste already deposited in the bag 54 to find the objects. By detecting the waste in batches, i.e., batch processing, the amount of waste that requires inspection to find the metal-containing objects is much smaller. This makes it easier to sort through and reduces exposure to harmful contaminates, offensive odors, broken glass or other objects that could be a hazard to the individual required to sort through the waste stream.

The pre-detection apparatus of FIG. 5 includes a hopper 200 rotatably connected to the frame 50. Hopper 200 includes a support platform 202, a pair of sidewalls 204 extending upwardly from the support platform 202, and a rear wall 203 extending upwardly from the support platform 202. The rear wall 203 interconnects the sidewalls 204 to form a temporary storage space 205 for each batch of waste to be processed. A pair of hinges 206 pivotally connects the platform 202 to the frame 50. The hopper 200 pivots about the hinges 206 between a load position and a dump position. The user grasps a handle 208 on the hopper 200 to move the hopper 200. An arm 210 extends perpendicularly in a cantilevered fashion from the leg 48 to support the hopper 200 and each batch load.

In this embodiment, a second pressure-sensitive transducer 211 is disposed on the arm 210 to determine the weight of each batch of waste. This information can be used to develop a metal content-to-weight ratio or factor. Accordingly, the alarm could be based on this factor. For instance, the segments 87 on the light bar 85 could be selectively illuminated based on this ratio being above a predetermine level.

In this embodiment, the coils 70, 72, 73 are disposed in the sidewalls 204 to detect metal that may be present in each batch. The metal detection arrangements previously described could be utilized, such as the concentric coil arrangement, which could be placed in the platform 202. It should also be appreciated that any metal detection arrangement could be employed with any of the pre-detection features described herein.

During use, objects intended for disposal in the bag 54 are first placed on the support platform 202 of the hopper 200. Support platform 202 thus functions as a loading station for the waste. Metal detection continues while each object is loaded into the hopper 200. When metal is detected, as previously described, the audible alarm, the visual alarm or both alarms are actuated. By using the hopper 200, the worker has less waste to sift through when metal is detected. Likewise, the batch load has a relatively small depth such that the user can often visually inspect the waste when the alarm is actuated to find the metal-containing object that tripped the alarm. Once the user is satisfied that material in the hopper 200 is to be discarded, the user grabs the handle 208 and moves the hopper to the dump position to allow gravity to transfer, dump, the batch in the bag 54.

Figure 7:
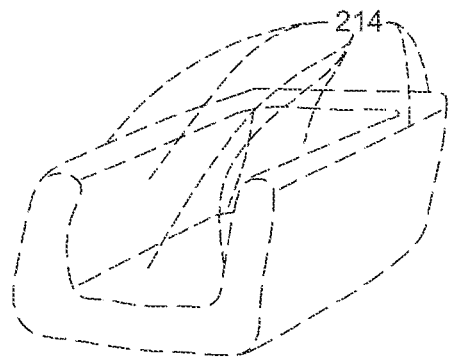
FIG. 7 is a perspective view of a protective covering for use with a hopper of FIG. 5.
Figure 8:
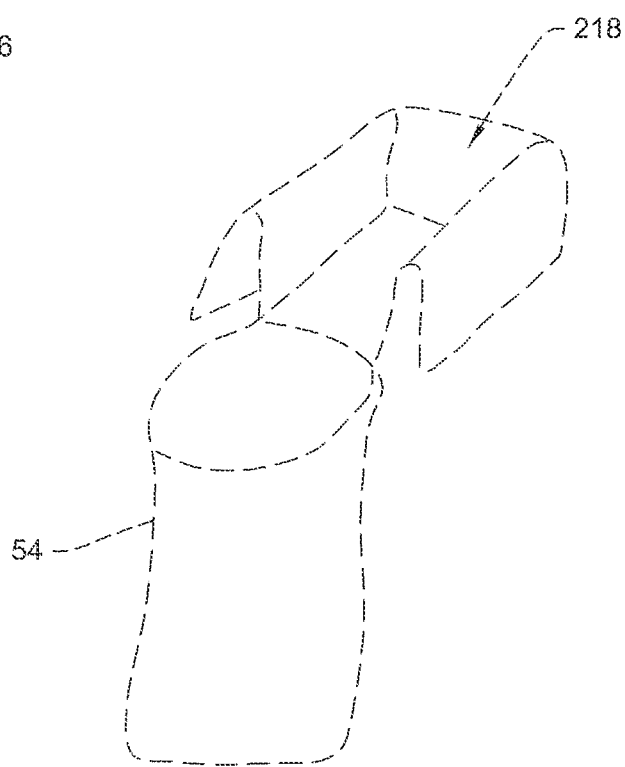
FIG. 8 is a perspective view of an alternative bag/covering for use with the cart and hopper of FIG. 5.

Referring to FIGS. 5 and 7, a separate disposable covering 212 protects the hopper from being soiled by the waste. The covering 212 defines a sleeve that slips down over the rear wall 203 and sidewalls 204 of the hopper 200. The sleeve includes a plurality of panels 214 sealed together to form an air-tight barrier that closely follows the shape of the hopper 200. FIG. 8 shows a bag 216 with an alternative protective covering 218 for the hopper 200 integrated with the bag 54 previously described.

Referring to FIG. 9, an alternative system 340 of this invention with a pre-fill structure includes a platform 300 pivotally connected to the frame 50. A pair of hinges 302 pivotally connects the platform 300 to the frame 50. The platform 300 is movable between a stowed position in which the platform folds down to reduce the overall footprint of the cart 342 and a load position (shown in FIG. 9).

A disposable tray 304 (or reusable tray with protective covering) is disposed on the platform 300 when in the load position for receiving waste intended for depositing in the bag 54. Platform 300 functions as the loading station.

A detector frame 306 slides along the platform 300 either manually or automatically to scan the tray 304 when full to determine if any metal-containing objects not to be discarded are present. The detector frame 306 includes four interconnected members 308, 310, 312, 314 including opposing top 308 and bottom 310 members and opposing left 312 and right 314 side members. The side members 312, 314 are notched to slidably receive the platform 300. The coils 70, 72, 73 are disposed in the side members 312, 314 to detect any metal-containing objects.

In embodiments in which scanning is automatic, the platform 300 includes a second pressure-sensitive transducer 316 to determine the weight of the batch of waste on the tray 304. When the batch reaches a predetermined weight or metal content-to-weight factor, the detector frame 306 moves across the tray to detect any metal-containing objects.

A drive assembly 318 moves the detector frame 306. The drive assembly 318 includes a motor 320 and a drive screw 322. The drive assembly 318 further includes a drive nut 324 fixed to the bottom member 310 to receive the drive screw 322. Preferably, the processor 74 actuates the motor 320 upon the batch reaching the predetermined weight. Alternatively, the processor actuates the motor 320 periodically to scan the batch with the drive assembly 318 re-setting the detector frame 306 to the start position (see FIG. 9) at the end of each scan. The motor 320 could also be push-button controlled in manual embodiments. A manual wand metal detector 326 could also be used to scan the batch of waste before dumping in the bag 54.

In a similar embodiment shown in FIG. 10, a detector frame 330 is fixed to the platform 300 of the cart 42 and the user passes the tray 304 through the detector frame 330 prior to disposal. When the user is satisfied that the detected objects were not inadvertently discarded, the user manually dumps the tray in the bag 54.

Figure 11:
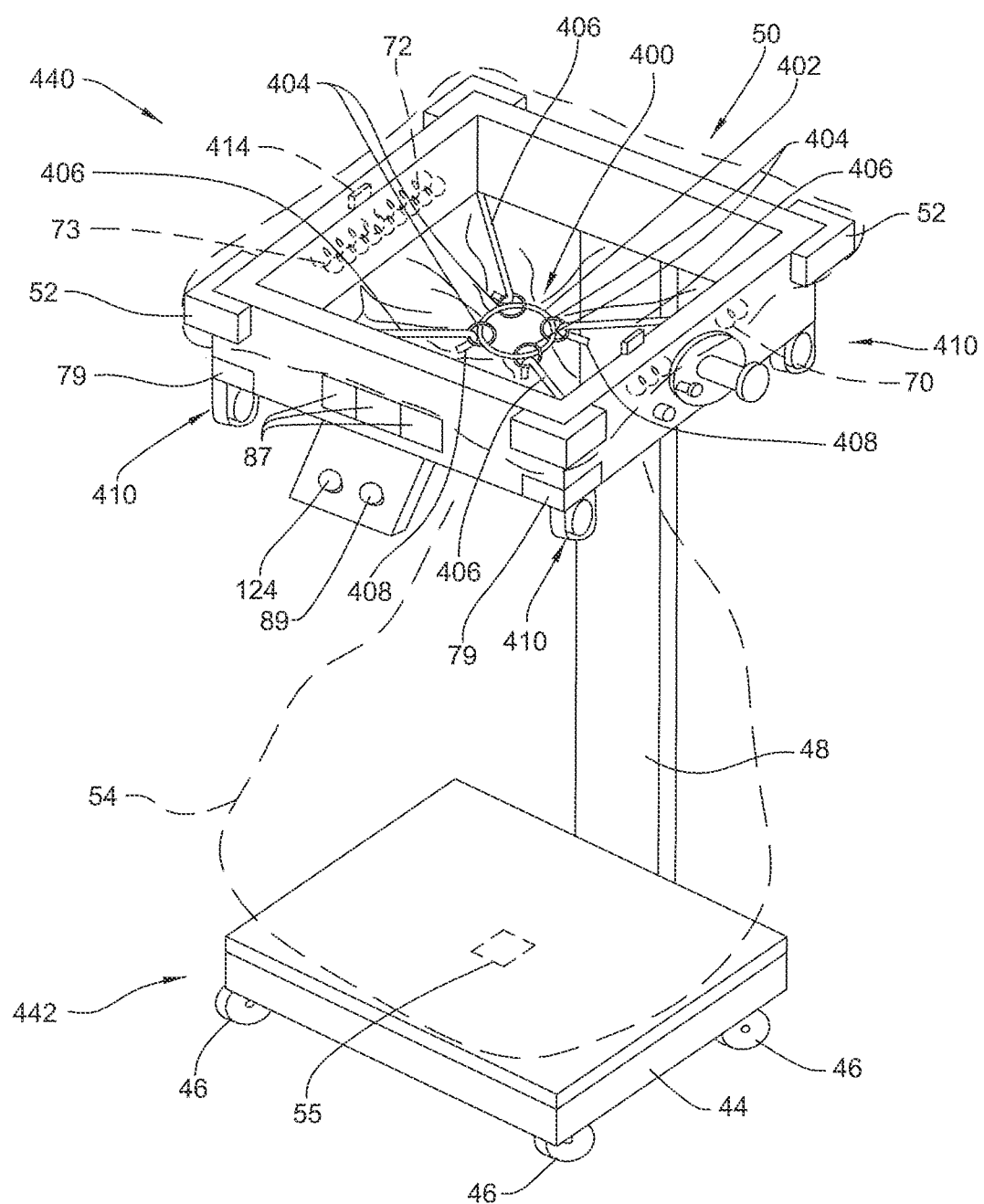
FIG. 11 is a front perspective view of the cart with another pre-detection apparatus.
Figure 12:
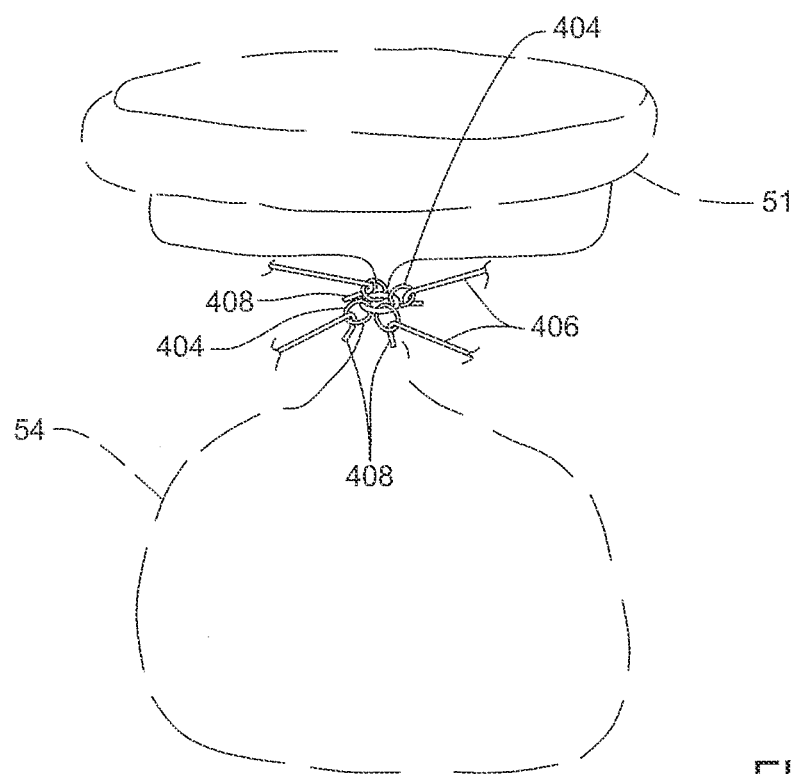
FIG. 12 is a side perspective view of a bag and bag-constraining device used with the cart of FIG. 11.
Figure 13:
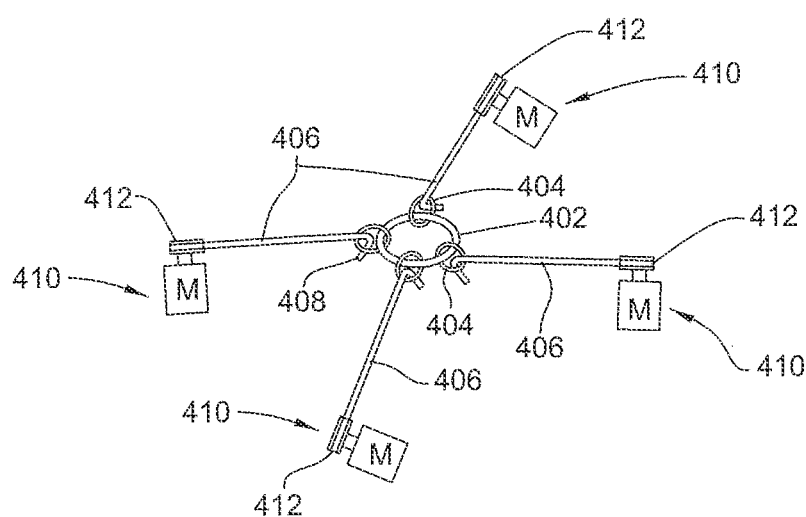
FIG. 13 is a top view of the bag-constraining device.

Referring to FIG. 11-13, another system 440 with a pre-detection apparatus is shown. In this embodiment, a bag-constraining device 400 chokes the bag 54 just below the frame 50 to create a batch volume in the bag 54. The bag-constraining device 400 includes an elastic band 402 placed over the bag 54 at the desired position. In its normal state, the elastic band 402 chokes the bag 54 to prevent the transfer of waste from above the band to below the band until each batch is processed. Typically, the batch volume is sized such that two to ten batches are processed for each bag 54.

The bag-constraining device 400 also includes a plurality of non-metal loops 404 each of which extends around the band 402. A flexible, non-elastic cable 406 extends from each of the loops 404 and is connected to the loops 404 with hooks 408 or Velcro™ or other releasable connector. A plurality of motor/pulley assemblies 410 operate to wind each of the cables 406 on pulleys 412 (see FIG. 13). When winding the cables 406 on the pulleys 412, the elastic band 402 is pulled at four equidistant positions around the band 402 to expand the band 402 and unconstrain the bag 54 to release the batch contents.

During operation, the upper portion of the bag 54, when in the constrained state, functions as the loading station in which the material intended for disposal is initially deposited. The height of the material in this loading station is monitored by an optical sensor 414 mounted in one of the webs 60, 62, 64, 66. This material height measurement serves as an approximation of the volume of waste at the station. Once the height of the waste reaches the optical sensor, the processor 74 determines the cumulative content of the metal sensed in the batch of material at the loading station. If the calculated metal content is within an acceptable limit, processor 74 allows the material to fall into the bottom section of the bag 54. Processor 74 allows this event to occur by actuating the motor/pulley assemblies 410 to expand the elastic band 402 and release the batch load of waste. Once the load is released, the motor/pulley assemblies 410 reverse direction and the elastic band 402 is allowed to re-choke the bag 54 in preparation for a new batch of waste. It should be appreciated that a manual push-button control could also be used to actuate the motor/pulley assemblies 410. Coils 70, 72, 73 are disposed in the frame 50 to detect metal in each batch and actuate the alarm as previously described.

The bags 54 can be assembled and provided to the facility in which the procedure is being performed with the band 402 and loops 404 already attached to the bags 54. This way the user has only to connect or disconnect the hooks 408 to the band 402 when replacing bags 54. With the band 402, a smaller footprint is provided to take up less floor space than other embodiments of the invention.

Figure 14:
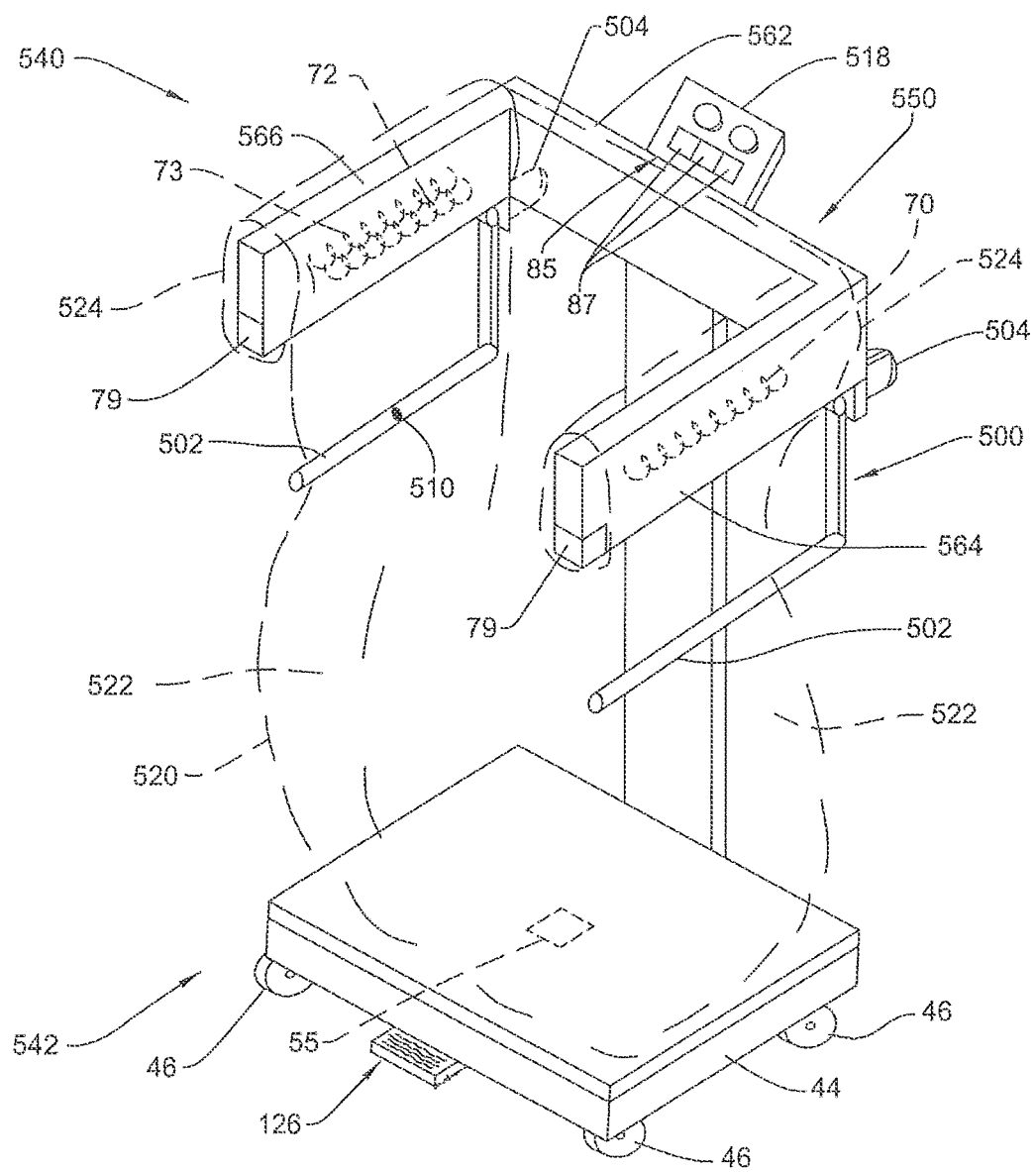
FIG. 14 is a front perspective view of the cart with another bag-constraining device comprising pivoting pinch bars.
Figure 15:
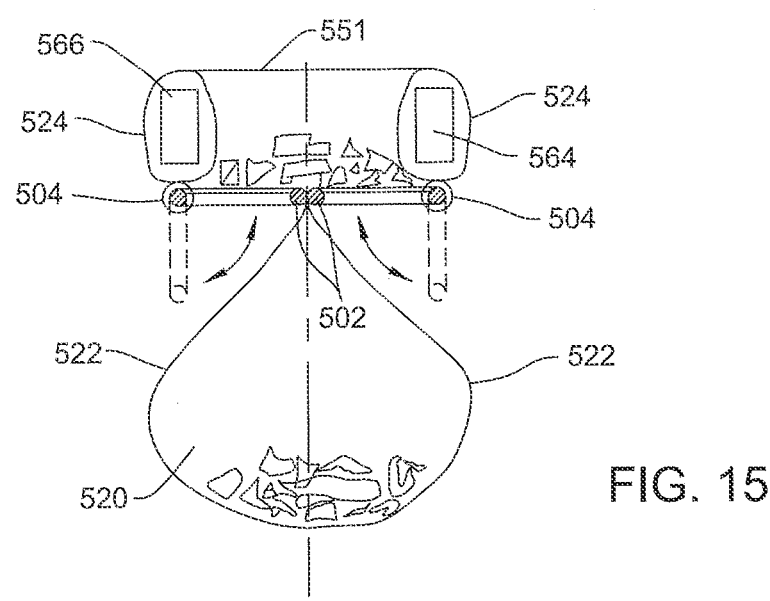
FIG. 15 is a front elevational view of the bag of FIG. 14 illustrating the pinch bars in a load position.
Figure 16:
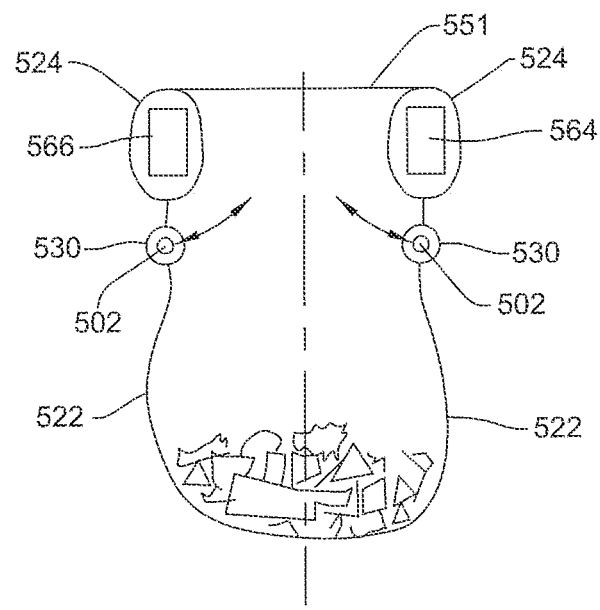
FIG. 16 is a front elevational view of the cart of FIG. 14 illustrating the pinch bars in a dump position.

Referring to FIGS. 14-16, another system 540 including a cart 542 is shown with an alternative bag-constraining device 500. Here, the band 402 is replaced with a pair of pinch bars 502 to create the batch volume in the bag 54. A pair of motors 504 are mounted to an underside 506 of corners of frame 550. Each motor 504 operates one of the pinch bars 502 to close and pinch the bag 54 just below the frame 550. Coils 70, 72, 73 are disposed in the frame 550 to detect metal. A second pressure transducer 510 is disposed on one of the pinch bars 502 to detect the batch weight. The processor 74 assesses the weight and the metal content of the batch, and if acceptable, the pinch bars 502 are moved automatically to release the batch into the lower portion of the bag 54.

In this embodiment, the frame 550 is modified by removing the front web 60 and corner blocks 52. Instead, the frame 550 of FIGS. 14-16 includes only a rear web 562 and side webs 564, 566. The lights 79 are mounted to the end of the side webs 564, 566 and on a display board 518. FIG. 15 shows a bag 520 configured to fit onto the cart 542 shown in FIG. 14. Like the bag 54 of FIG. 1, bag 520 is formed of two main rectangular panels 522 sealed together at their bottom and side edges. The bag 520 further includes a pair of sleeve panels 524 sealed at their top edges 551 and bottom edges (not identified) to the outside of the main panels 522 at the top of each of the main panels 522 and just below the top of each of the main panels 522 to define sleeves for sliding onto the side webs 564, 566. The sleeves protect the side webs 564, 566 from dust and debris during use.

FIG. 16 shows another bag with a second pair of sleeve panels 530 sealed to the outside of the main panels 522 to define sleeves for sliding onto the pinch bars 502. The second pair of sleeve panels 530 are also sealed along their top and bottom edges across each of the main panels 522. The sleeve panels 524, 530 have a length equal to a width of the main panels 522 such that the top and bottom edges of the sleeve panels 524, 530 are sealed completely across the main panels 522, while the side edges of the sleeve panels 524, 530 remain unsealed to provide the sleeves for slipping on the side webs 564, 566 and pinch bars 502.

In the versions of the invention illustrated with respect to FIGS. 14-16, as with the versions of the invention illustrated in FIGS. 11-13, the top of the bag, when in the constrained state, functions as the loading station on which the material deposited for disposal is initially placed.

Figure 17:
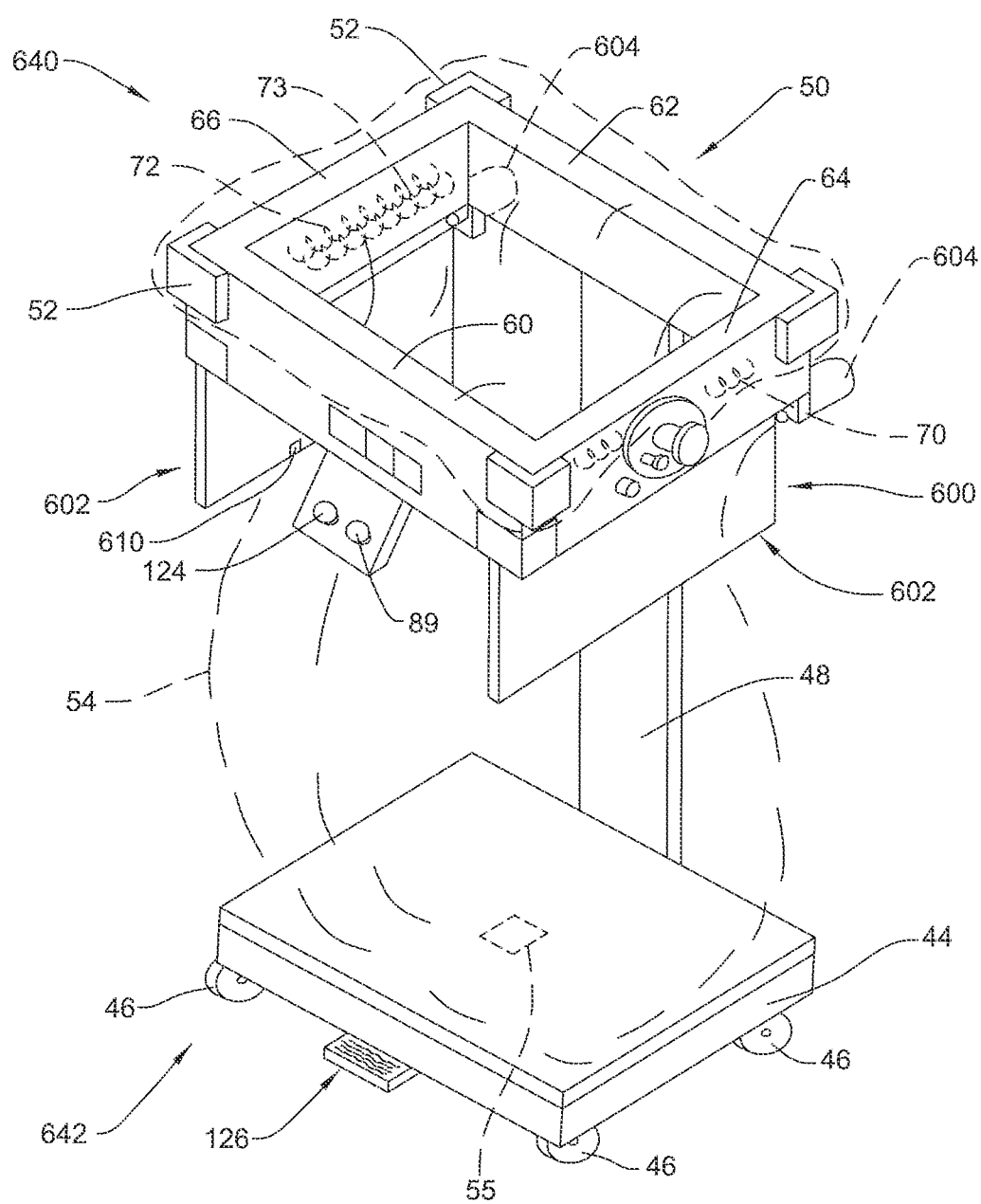
FIG. 17 is a front perspective view of another cart with yet another bag constraining assembly comprising pivoting doors.

Referring to FIG. 17, another system 640 with a cart 642 with a bag-constraining device 600 is shown. In this embodiment, the bag-constraining device 600 includes a pair of doors 602 pivotally mounted to the side webs 564, 566. The doors 602 are moveable between dump positions and load positions. Each door 602 is generally planar to form a bottom of the frame 50 when in the load position. A pair of motors 604 are mounted to an underside of the rear corners of the frame 50. Each motor 604 rotates one of the doors 602 between the dump position and the load position. In the load position, the doors 602 close an opening through the frame 50 and pinch the bag 54 therebetween. After a new bag 54 is placed on the cart 642, the motors 604 automatically or manually move the doors 602 to the load position.

Once in the load position, the cart 642 is ready for batch loading. Coils 70, 72, 73 are disposed in the frame 50 to detect metal. A second pressure transducer 610 is disposed on one of the doors 602 to detect the batch weight. The doors 602 are moved automatically upon the batch reaching a predetermined weight or metal content-to-weight factor. The batch loading, alarming and dumping processes proceed in this embodiment as described in the previous embodiments including both manual and automatic operations.

Figure 18:
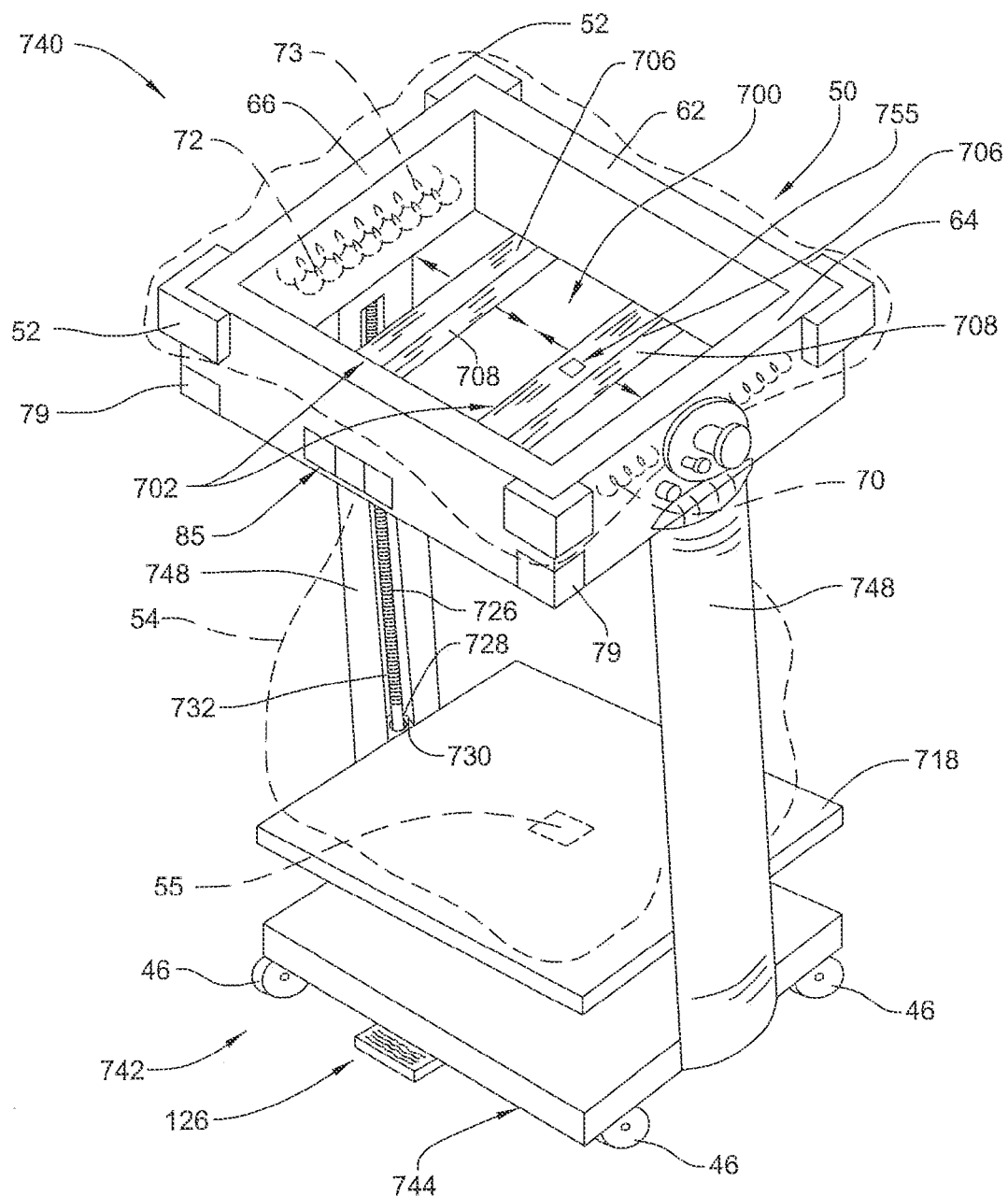
FIG. 18 is a front perspective view of an alternative cart with a movable platform and pinch bar assemblies with heat-sealing coils to segment the bags into separate sealed batches of waste.
Figure 19:
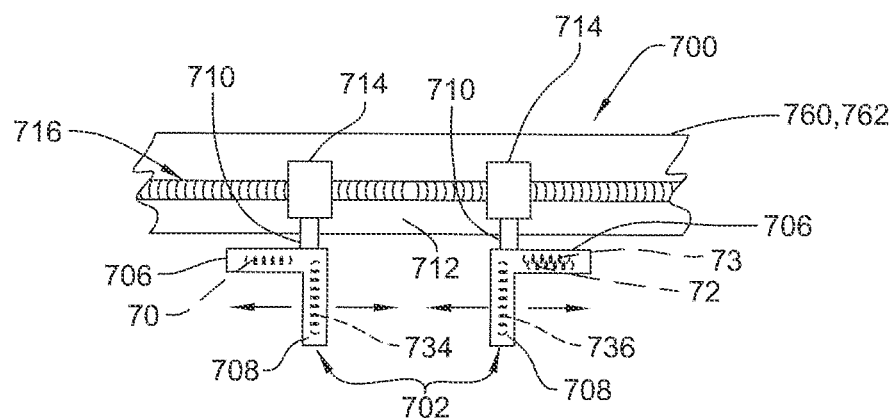
FIG. 19 is an elevational view of the pinch bars and drive assembly of the cart of FIG. 18.
Figure 20:
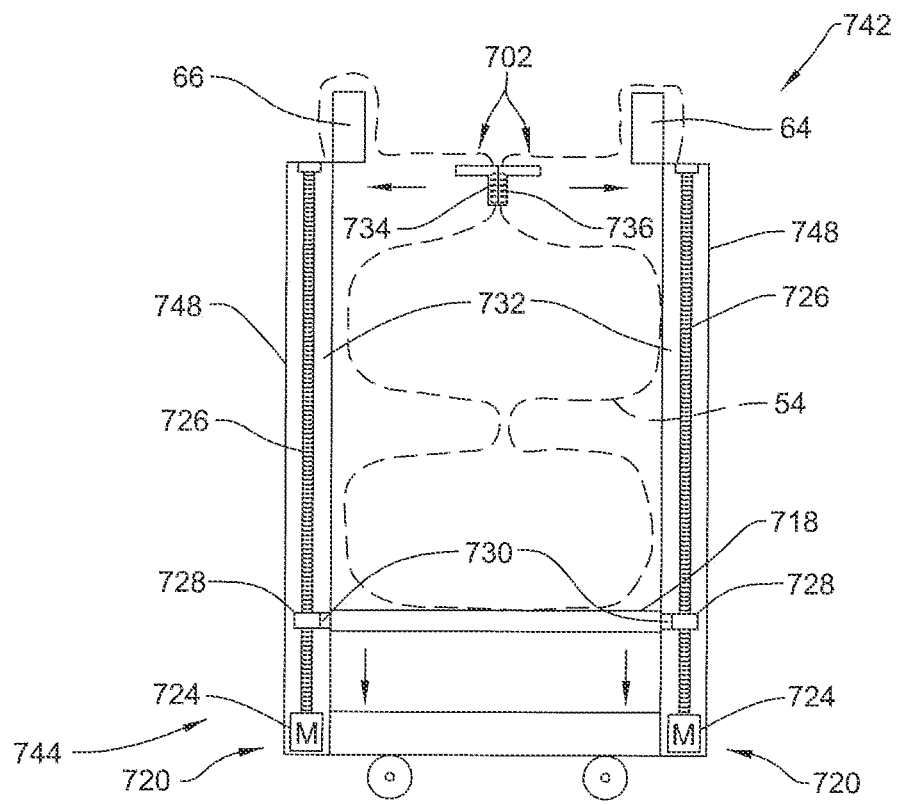
FIG. 20 is a front elevational view of the cart of FIG. 18 illustrating several sealed batches of waste.

FIGS. 18-20 show another system 740 with a cart 742 with a bag-constraining device 700. In this embodiment, the bag-constraining device 700 pinches the bag 54 just below the frame 50 and heat seals the bag 54 at this location to create a batch volume for the waste of only a portion of the total volume of the bag 54. Preferably, two to ten batches are processed in each bag 54.

Referring specifically to FIG. 19, the bag-constraining device 700 includes a pair of pinch bar assemblies 702 for pinching the bag 54 just below the frame (frame not identified). Each pinch bar assembly 702 includes a horizontal member 706 and a vertical member 708 extending downwardly from the horizontal member 706. A rectangular key 710 is disposed on each opposing end of the horizontal member 706 and extends upwardly from each end through an elongated slot in the underside of the front 760 and rear 762 webs (slots not illustrated). A nut 714 is fixed to each of the keys 710. A drive screw 716 is mounted in each of the front 760 and rear 762 webs to drive the nuts 714 while the keys 710 in the slots 712 prevent the nuts 714 from rotating. The nuts 714 travel along the drive screw 716 to move the pinch bar assemblies 702 from the dump position to the load position. The drive screw 716 can be configured such that one half of the drive screw 716 has threads in one direction and one half with threads in an opposite direction. Drive screw 716 thus moves nuts 714 of pinch bar assemblies 702 toward one another when the drive screw is rotated in one direction and away from one another when rotation is reversed.

Referring to FIG. 20, the base 744 of the cart 742 includes a movable platform 718 for supporting the bag 54 and its contents. A pair of drive assemblies 720 move the movable platform 718 upwardly along two rectangular legs 748. Each drive assembly 720 includes a motor 724 mounted to the base 744 and a drive screw 726 rotatably supported in each of the legs 722. The movable platform 718 includes a pair of drive nuts 728 fixed to and extending from opposing sides of the movable platform 718. Keys 730 connect the nuts 728 to the movable platform 718. The keys 730 are inserted into elongated slots 732 in the legs 748 to travel along the slots 732 during adjustment that is similar to the pinch bar assemblies 702.

When a bag 54 is first placed on the cart 742, the pinch bar assemblies 702 are moved to the load position to constrain the bag 54 below the frame 750 and the movable platform 718 is raised to a position just beneath the pinch bar assemblies 702. When the pinch bars 702 close, the opposed sections of the bag above the pinch bars is become a loading station. Material for disposal is placed on these sections of the bag 54. The coils 70, 72, 73 may be disposed in side webs 64, 66 as previously described, or the coils 70, 72, 73 may be disposed in the horizontal members 706 of the pinch bar assemblies 702. Metal detection and alarms occur as previously described in this embodiment.

Once the initial batch of waste is processed, the pinch bar assemblies 702 either manually or automatically are moved from the load position to the dump position. The movable platform 718 supports the batch load. Platform 718 is then lowered until the pinch bar assemblies 702 are disposed above the batch load.

Heat-sealing coils 734, 736 are disposed in the vertical members 708 of the pinch bar assemblies 702. The vertical members 708 come together in the load position for the second batch of waste and the processor 74 then actuates the heat-sealing coils 734, 736 to create a seal at a pinched section of the bag 54 above the initial batch load.

Thus, the bag 54 is sealed above and below the batch load to contain fluids and reduce odors from emanating out of the bag 54. In this embodiment, the initial batch load is stored at a bottom of the bag 54. Bag 54 is then heat sealed above the batch load. Subsequent batches are stored on top of the previously stored and sealed batches. The movable platform 718 may include the transducer 55 so that the processor 74 can determine an overall weight of the bag 54. Alternatively, a second transducer 755 on one of the pinch bar assemblies 702 may be used to determine batch weights and total weight by adding individual batch weights. The second transducer 755 can also be used for determining, by the processor 74, when each batch is finished processing using weight or factor values.

In other embodiments, heat sealing could be replaced by batch separators that are either manually or automatically placed in the bag 54 to separate batch loads, e.g., cardboard inserts (not shown), or the bags 54 could be configured with integral flaps (not shown) that fall into place over each batch after each batch is processed.

Figure 21:
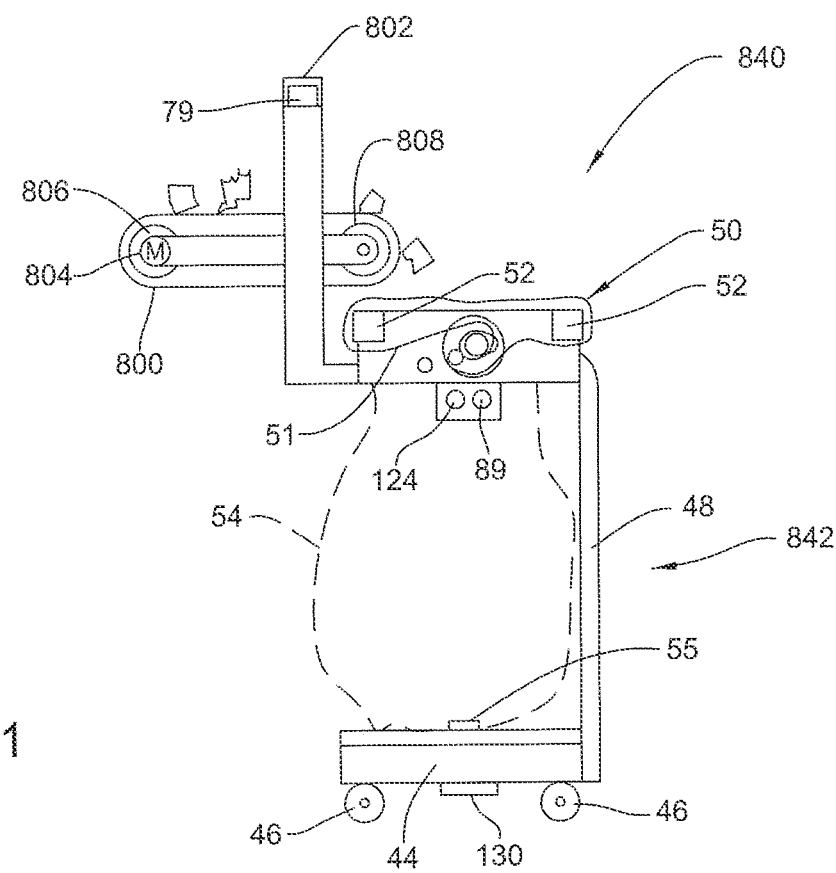
FIG. 21 is a front perspective view of another cart outfitted with a conveyor belt for moving waste through a metal detector frame and into the bag.

Referring to FIG. 21, an assembly 840 with a cart 842 similar to that shown in FIG. 10 is shown with a conveyor belt 800 spaced away from the open end of the bag 54. Conveyor belt 800 thus functions as the loading station on which the material for disposal is placed. A frame 802 with metal detecting sensors is located over the conveyor belt 800. A motor 804 and motor-driven roller 806 drives the conveyor belt 800 around a second roller 808. The material deposited for disposal initially passes across the metal-detecting sensors located in frame 802. From frame 802, conveyor belt 800 transfers the material into the open end of the bag 54. If, however, the sensors assert signals indicating the potential presence of the metal, the processor controlling assembly 840 asserts one or more alarms to provide notice of the possibility of an object in the waste stream that should not be disposed. The processor also deactivates the motor 804 to stop the object from being dumped into the bag. This gives personnel the opportunity to inspect the object to determine whether or not the object should be disposed. This embodiment could also include doors (not shown) to open and close access to the bag 54. In this embodiment, waste is placed on the conveyor belt which closely simulates the process of throwing trash directly into a bag. This embodiment closely matches what is traditionally done in medical facilities today, namely discard trash at the point of generation and therefore causes minimal disruption to the medical procedure.

Figure 22:
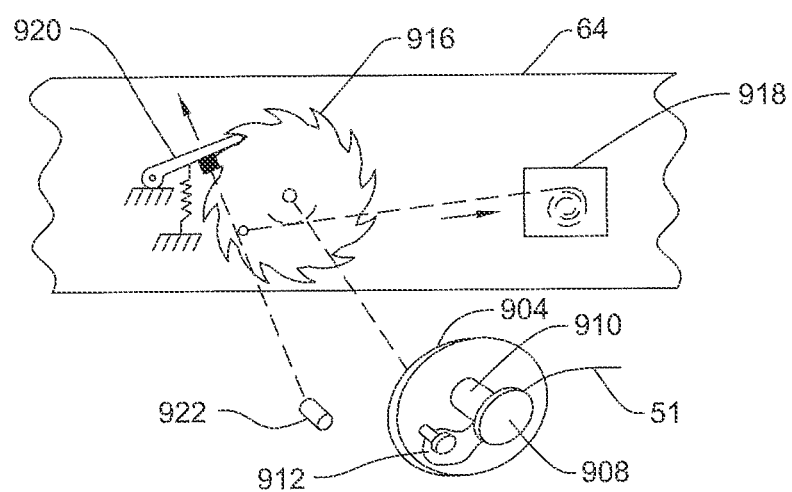
FIG. 22 is a front partially perspective view of a bag-tensioning mechanism of the cart of FIG. 1.

Referring to FIGS. 1 and 22, a bag-tensioning mechanism 900 is shown. The bag-tensioning mechanism 900 includes a knob 902 rotatably mounted to and supported in one of the side webs 64, 66. The knob 902 includes a base plate 904 in rotating abutment with an outer side face 906 of, arbitrarily, side web 64. An outer grasping head 908 is spaced from the base plate 904 by a shaft 910. A bag catch 912 is mounted to the base plate 904 and extends outwardly therefrom for catching a portion of the periphery 51 of the bag 54. The bag catch 912 is preferably a pin. The pin 912 may include an enlarged head spaced from the base plate 904 in order to retain the periphery 51 of the bag 54 to the pin 912.

Referring specifically to FIG. 22, inside a hollow space of the side web 64, the knob 902 includes a ratchet plate 916. The ratchet plate 916 is spring loaded by a spring 918 so that as the ratchet plate 916 is rotated, the spring tension force increases. A spring-biased pawl member 920 ratchets along notches in the ratchet plate 916 to hold the ratchet plate 916 against the spring tension force and the external forces generated from the bag periphery 51 tension. A release push button 922 is arranged to lift the pawl member 920 when pressed and release the ratchet plate 916. When this occurs, the ratchet plate 916 and knob 902 rotate back to their initial position under the spring tension force placed on the ratchet plate 916 and knob 902 by the spring 918.

In use, the bag 54 is first folded over the corner blocks 52. A portion of the folded over periphery 51 of the bag 54 is routed around the shaft 910 and wrapped or hooked about the bag catch 912. The top 2.5 to 5 cm of the folded over periphery 51 of the bag is wrapped about the bag catch 912. The user rotates the knob 902 by grasping the grasping head 908 of the knob 902 to twist the periphery 51 of the bag 54 and tension the periphery 51 of the bag 54. This tension secures the bag 54 by increasing the friction between the bag 54 and the frame 50 as well as increasing the hoop tension below the corner blocks 52 thus working in combination with the corner blocks 52 to secure the bag periphery 51 around the outside of the side webs. Dislocating the bag from this tensioned position requires the bag 54 to stretch over the corner blocks 52. To release the bag 54, the user presses the release button 922. The release button 922 allows the bag 54 to become untwisted relieving the tension on the periphery 51 of the bag 54. The knob 902 automatically returns to its home position, via the spring 918 and the user can then pull the bag 54 off the bag catch 912 and uncoil the twisted bag 54 from the shaft 910 of the bag-tensioning mechanism 900. The bag-tensioning mechanism 900 is now ready for a new bag 54.

Figure 23:
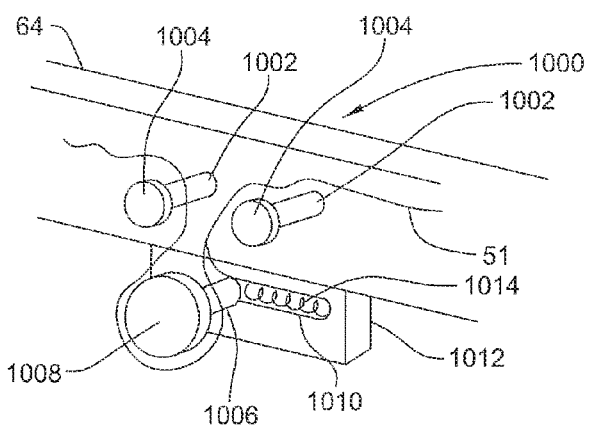
FIG. 23 is a front perspective view of an alternative bag-tensioning mechanism with a sliding pin for placing tension on a periphery of the bag.

Referring to FIG. 23, an alternative bag-tensioning mechanism 1000 is shown. In this embodiment, two routing posts 1002 with enlarged heads 1004 are mounted to one of the side webs 64, 66. A spring-loaded sliding pin 1006 with enlarged head 1008 acts to tension the periphery 51 of the bag 54. The pin 1006 is slidably mounted through an elongated slot 1010 in a housing 1012 mounted to an underside of the side web 64. A spring 1014 is mounted to the pin 1006 at one end and to the housing 1012 at an opposite end. The user first positions the sliding pin 1006 to a load position by overcoming the spring tension (as shown in FIG. 23). The periphery 51 of the bag 54 is routed between the routing posts 1002 and over the enlarged head 1008 of the sliding pin 1006. The user then releases the sliding pin 1006 and the periphery 51 of the bag 54 is tensioned holding it onto the corner blocks 52 with increased friction and hoop tension as described earlier. To release the bag 54, the user re-positions the sliding pin 1006 into the load position and unhooks the bag 54 from the sliding pin 1006. The enlarged heads 1004 of routing posts 1002 and head 1008 of pin 1006 keeps the periphery 51 of bag 54 from slipping off of those components.

Figure 24A:
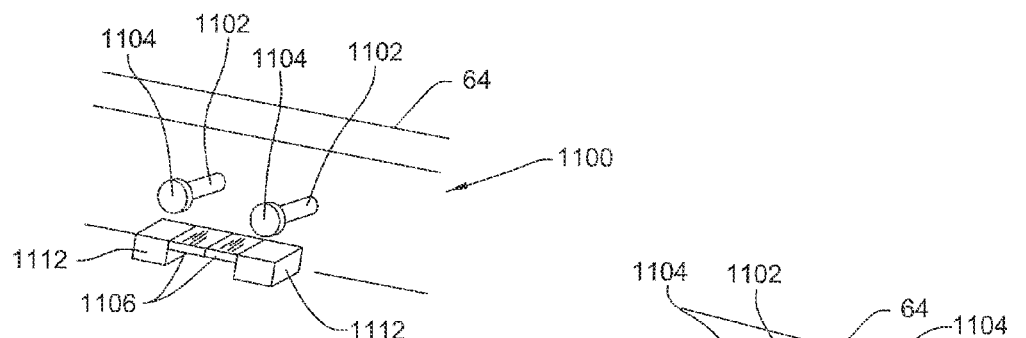
FIGS. 24A, 24B and 25 are front perspective views of further alternative bag-tensioning mechanisms utilizing flexible gripping pads for gripping the bag to hold its tension on the frame of the cart.
Figure 25:
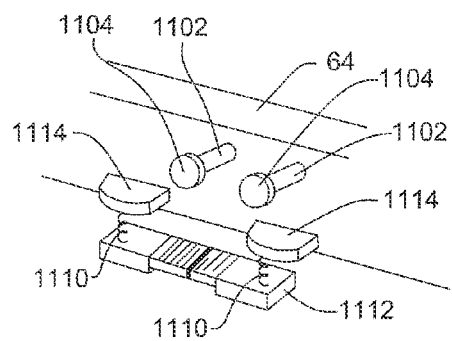
Figure 24B:
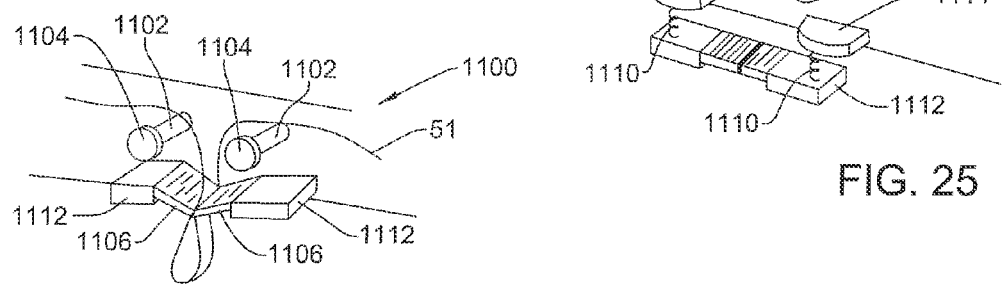

Referring to FIGS. 24A, 24B and 25, another alternative bag-tensioning mechanism 1100 is shown. Here, two routing posts 1102 with enlarged heads 1104 are mounted to one of the side webs 64, 66. A pair of mounting brackets 1112 are fixed to the side web 64. A pair of rubber gripping pads 1106 are mounted to the brackets 1112 beneath the routing posts 1102. The pads 1106 are fixed at one end to the brackets 1112 and extend to a cantilevered end such that the cantilevered ends of the pads 1106 abut one another. The periphery 51 of the bag 54 is routed between the routing posts 1102 and between the cantilevered ends of the pads 1106. The pads 1106 flex downwardly as a portion of the periphery 51 of the bag 54 is pulled between the pads 1106. Once enough tension is placed on the bag 54 to hold the periphery 51 to the frame 50, the user ceases pulling the bag 51 through the pads 1106. The pads 1106 then release toward their normal position horizontally opposed to one another and pinch the bag 54 between the pads 1106 to hold the bag 54 in place as shown in FIG. 24B. The pads 1106 and brackets serve as a one-way holding mechanism to maintain the periphery 51 tension applied by the user. To release the bag periphery 51, the user pulls the bag horizontally, parallel to the pads 1106 edges until the bag periphery 51 if clear of the pads 1106.

In the variation shown in FIG. 25, springs 1110 extend from projections 1114 fixed to the web 64. The springs 1110 movably connect the brackets 1112 to the projections 1114. The springs 1110 urge the pads 1106 upwardly as the user pulls the bag through the pads 1106 downwardly to facilitate mounting of the bag 54.

Figure 26:
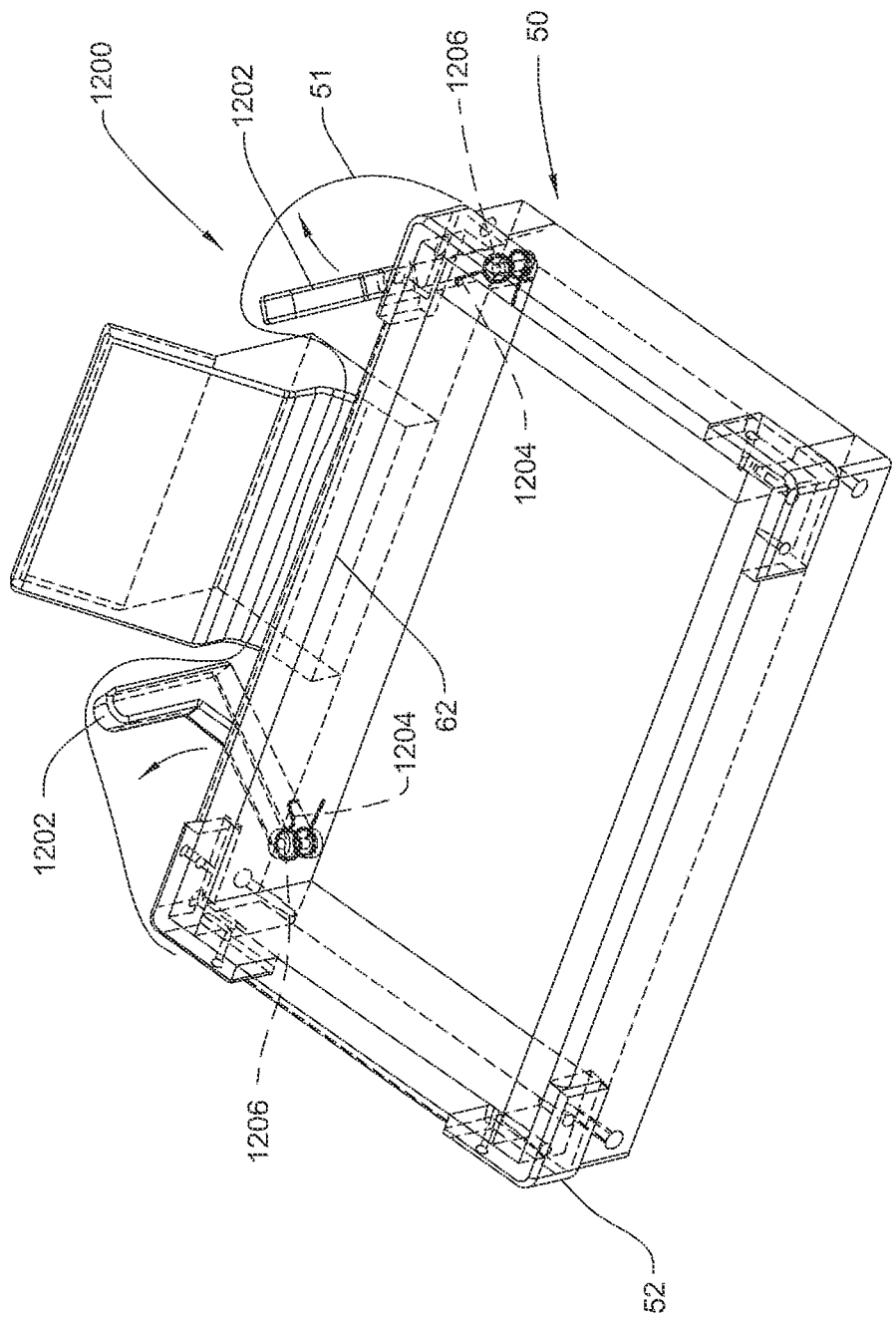
FIG. 26 is a top perspective view of yet another bag-tensioning mechanism comprising spring-biased swing arms.

FIG. 26 shows another bag-tensioning mechanism 1200. In this embodiment, two swing arms 1202 are pivotally mounted to the rear web 62 of the frame 50. Torsion springs 1204 are positioned over pins 1206 that pivotally hold the swing arms 1202 to the rear web 62. The swing arms 1202 are L-shaped. Springs 1204 place a force on arms 1202 that normally hold the arms away from rear web 62. In use, the periphery 51 of the bag 54 is rolled over the frame 50 and the swing arms 1202 while the swing arms 1202 held against the rear web 62 and against the spring bias of springs 1204. The swing arms 1202 are then released. The force of the springs 1204 moves the arms 1202 outwardly. The outward movement of the arms against the bag places a tension on the periphery 51 of the bag 54. To remove the bag 54, the swing arms 1202 are again held against the frame 50 and the bag 54 is removed from the frame 50 and swing arms 1202.

In other versions of the invention not shown, a supplemental identification system could be used in combination with metal detection to prevent re-usable objects from being discarded, or to prevent objects from being discarded in the wrong bag. Referring to FIG. 1, the identification system includes RFID tags 90 (see sample object being discarded) placed on all objects used during the course of a medical or surgical procedure. A reader 88 mounted to the frame senses the RFIDs as they pass by the reader 88 while discarded. In FIG. 1, the reader 88 is mounted to the rear web 62 and an object with RFID 90 is shown passing the reader 88. The reader 88 sends corresponding signals to the processor 74 when each RFID is sensed. The processor 74 then looks up the RFID in look-up tables to determine if the object is to be discarded or if it is reusable. If it is not to be discarded, the alarm is actuated. A different alarm could be used to clearly indicate that the object was incorrectly discarded.

The processor 74 could also be wirelessly connected to a central inventory control system (not shown) to monitor inventory and order equipment, tools, accessories, etc. as the objects are discarded. At least two acceptable modes of wirelessly transmitting data from the processor to the inventory control system are Infrared or Radio frequency. In one example, the packaging materials of a single use disposable product can contain the RFIDs and the reader 88 transmits the signal to the central inventory control system indicating the package has been opened and needs replacement.

The data from the RFID tag and other metal detection information can be wirelessly transmitted to other management systems that may benefit from such information.

During the course of a procedure the waste is deposited in the corresponding bags 54 (e.g., white, red, green, yellow, etc.) secured to separate carts 42. The carts 42 are typically positioned in the operating room or other space in which waste are generated. A circulating nurse, or other individual that receives the waste from the person depositing it, is responsible for initially categorizing the waste and placing it in the appropriate cart 42. When a bag 54 containing either conventional waste, red bag waste, green waste or radioactive waste is at or near capacity, it is sealed. At that time, the bag 54 is transported to a loading dock for eventual transport to a waste processing facility.

Obviously many modifications and variations of the present invention are possible in light of the above description. Thus the features of the different embodiments of this invention may be combined. Also, not all features in each embodiment of the invention may be necessary to provide the advantages and benefits of the described embodiments. Similarly, the shapes of the components may be different from what has been described. For example, while the frame from which the bag is suspended is generally shown as rectangular, it need not always have this shape. In some versions of the invention the frame may be circular or oval. In not all versions of the invention is it necessary to have a null coil as part of the metal detection assembly. Likewise other means than the disruption of magnetic fields may be used to sense whether or not there is metal in the object being subjected to disposal.

While this description is directed to particular embodiments, it is understood that those skilled in the art may conceive of modifications and/or variations to the specific embodiments shown and described herein. Any such modifications or variations, which fall within the purview of this description, are intended to be included herein as well. It is understood that the description herein is intended to be illustrative only and is not intended to be limited.

What is claimed is:

1. A portable cart for containing medical waste, the cart including:
   a mobile base, said base configured to hold a container capable of receiving waste;
   a frame attached to said base that is located above said base, said frame having an outer surface and an opening, the frame opening positioned above an open end of the container so that waste is disposed into the container through the frame opening;
   a sensor mounted to said frame that detects if metal is passed through the frame opening and that asserts a sensor signal when metal is passed through the frame opening, wherein said sensor generates the sensor signal so that the sensor signal varies as a function of the amount of metal passed through the frame opening;
   a light alarm connected to said base or said frame; and
   an audible alarm connected to said base or said frame;
   a processor attached to said cart, said processor being configured to:
      continuously receive from said sensor the sensor signal;
      based on a comparison between the sensor signal and a threshold signal, determine if a first object with a content of metal in excess of an acceptable content of metal has passed through the frame opening; and
      if said processor determines that a first object with a content of metal in excess of the acceptable content of metal has passed through the frame opening, actuate said audible alarm for a defined period of time; and actuate said light alarm until a user-generated command is received and, upon receipt of the user-generated command, negate the actuation of said light alarm,
      wherein, prior to said processor negating the actuation of said light alarm, said processor continues to, based on the comparison between the sensor signal and the threshold signal, determine if a second object with a content of metal in excess of the acceptable content of metal has passed through the frame opening and, if a second object with a content of metal in excess of the acceptable content of metal has passed through the frame opening, again actuate the audible alarm for the defined period of time.

2. The portable cart of claim 1, wherein:
a light bar is connected to said frame and said light bar has a plurality of individually actuatable light segments; and
said processor is further configured to actuate the number of light segments of said light bar as a function of the amount of metal that passes through the frame opening as represented by the sensor signal.

3. The portable cart of claim 1, wherein:
said frame is further configured to removably hold open the container; and
a tensioner is mounted to said frame, said tensioner having at least one member mounted to said frame that engages a portion of the container that extends over a surface of said frame so that at least a portion of the container is placed in tension around a section of said frame.

4. The portable cart of claim 3, wherein said tensioner includes:
at least one pin mounted to said frame at a fixed location around which a first portion of the container is wound; and
a catch that is moveably mounted to said frame around which a second portion of the container is placed, said catch being located relative to said at least one pin so that the movement of said catch with the second portion of the container mounted thereto places the first portion of the container in tension around said at least one pin.

5. The portable cart of claim 1, wherein said processor is further configured to:
continuously produce averages of the sensor signal each of which is an average of the sensor signal over a period of time; and
when an object is passed through the frame opening into the container, determine if the object has a content of metal in excess of the acceptable content by comparing the averages of the sensor signal to the threshold signal.

6. The portable cart of claim 1, further including a selector that allows a user to set the threshold signal that said processor uses to determine if an object with a content of metal in excess of the acceptable content of metal is passed through the frame opening into the container so that the user can set the acceptable content of metal for an object placed in the container.

7. The portable cart of claim 1, further including a battery mounted to said mobile base to power said audible alarm, said light alarm and said processor.

8. The portable cart of claim 1, further including a rechargeable battery mounted to said mobile base to power said audible alarm, said light alarm and said processor.

9. The portable cart of claim 1, wherein:
in addition to said light alarm, a light bar is connected to said frame and said light bar has a plurality of individually actuatable light segments; and
said processor, in addition to, based on the comparison between the sensor signal and the threshold signal, selectively actuating the light alarm, is further configured to actuate the number of light segments of said light bar as a function of the amount of metal that passes through the frame opening as represented by the sensor signal.

10. A method of monitoring a container containing medical and surgical waste for the presence of metal in the container, said method including the steps of:
positioning a container on a base of a mobile cart, the mobile cart including: an audible alarm; a light alarm; a frame located above the container, the frame including a frame opening through which objects are passed into the container; and a sensor attached to the frame that detects if metal is passed through the frame opening into the container and that asserts a sensor signal when metal is passed through the frame opening into the container, wherein the sensor generates the sensor signal so that the sensor signal varies as a function of the amount of metal passed through the frame opening;
with a processing circuit attached to the mobile cart:
continuously monitoring the sensor signal;
comparing the sensor signal to a threshold signal level to determine if an object with a content of metal in excess of an acceptable content of metal has passed through the frame opening into the container;
if, as a result of said comparison, it is determined that a first object with a content of metal in excess of the acceptable content of metal has passed through the frame opening into the container, actuating the audible alarm for a defined period of time and actuating the light alarm;
when a user-generated command is received by the processing circuit, negating the actuation of the light alarm; and
prior to said step of negating the actuation of the light alarm, continuing to execute said step of comparing the sensor signal and the threshold signal level, and if, as a result of said comparison, it is determined that a second object with a content of metal in excess of the acceptable content of metal has passed through the frame opening into the container, again actuate the audible alarm for the defined period of time.

11. The method of monitoring a container containing medical and surgical waste of claim 10, wherein:
the mobile cart on which the container is positioned includes a light bar that has plurality of individually actuatable light segments; and
when the sensor signal indicates that metal passes through the frame opening, the processing circuit further performs a step of actuating a selected number of the light segments of the light bar, wherein the number of segments the processing circuit actuates is a function of the amount of metal that passes through the frame opening as represented by the sensor signal.

12. The method of monitoring a container containing medical and surgical waste of claim 11, wherein:
the light alarm and the light bar are separate components; and said steps of the processing circuit comparing the sensor signal to the threshold signal level and, based on the comparison, actuating the light alarm and said step of the processing circuit, based on the sensor signal, actuating a selected number of the light segments of the light bar are performed independently of each other.

13. The method of monitoring a container containing medical and surgical waste of claim 10, wherein in said step of positioning the container on the base of the mobile cart, the container is suspended from the frame so as to extend below the frame opening and, in said step of suspending the container from the frame, at least a portion of the container is placed around a moving component of a tensioner that is mounted to the frame so that the tensioner places the container in tension around at least a section of the frame.

14. The method of monitoring a container containing medical and surgical waste of claim 10, wherein:
with the processing circuit, continuously producing averages of the sensor signal, wherein each average sensor signal is an average of the sensor signal over a period of time; and in said step of comparing the sensor signal to the threshold signal level to determine if an object with a content of metal in excess of the acceptable content of metal has passed through the frame opening into the container, the processing circuit performs said comparison by comparing the averages of the sensor signal to the threshold signal level.

15. The method of monitoring a container containing medical and surgical waste of claim 10, further including the step of allowing a user to set the threshold signal level that is used by the processing circuit in said step of comparing the sensor signal to the threshold signal level to determine if an object with a content of metal in excess of the acceptable content of metal has passed through the frame opening into the container.

16. The method of monitoring a container containing medical and surgical waste of claim 10, further including the step of powering the processing circuit, the audible alarm and the light alarm with a battery attached to the mobile cart.

17. The method of monitoring a container containing medical and surgical waste of claim 10, further including the step of powering the processing circuit, the audible alarm and the light alarm with a rechargeable battery attached to the mobile cart.

\* \* \* \* \*